United States Patent [19]

Goodman et al.

[11] Patent Number: 5,660,980
[45] Date of Patent: Aug. 26, 1997

[54] METHODS FOR IDENTIFYING AND ISOLATING VARIANT T4 DNA POLYMERASES

[75] Inventors: Myron F. Goodman, LaCanada, Calif.; Linda J. Reha-Krantz, Edmonton, Canada

[73] Assignees: University of Southern California, Los Angeles, Calif.; University of Alberta, Edmonton, Canada

[21] Appl. No.: 465,995

[22] Filed: Jun. 6, 1995

Related U.S. Application Data

[62] Division of Ser. No. 101,593, Aug. 2, 1993, Pat. No. 5,547,859.

[51] Int. Cl.[6] .................................................. C12Q 1/70
[52] U.S. Cl. .................. 435/5; 530/358; 935/79; 935/82
[58] Field of Search ........................ 435/91.2, 5, 183, 435/235.1, 69.1; 530/358; 935/82, 79

[56] References Cited

PUBLICATIONS

Reha–Krantz et al., Proc. Natl. Acad. Sci., 88:2417–2421 Mar. 1991.

*Primary Examiner*—Scott W. Houtteman
*Attorney, Agent, or Firm*—Robbins, Berliner & Carson, LLP

[57] ABSTRACT

Method for identifying and isolating variant T4 DNA polymerase by isolating and selecting for T4 strains having variant DNA polymerase defective in DNA replication, and at least one additional mutation which corrects or compensates for said defect in DNA replication; identifying the additional mutation(s) and introducing the mutation(s) into T4 phage or T4 DNA polymerase expression vectors.

1 Claim, 6 Drawing Sheets

NUCLEOTIDE STRUCTURES

2'-DEOXYRIBONUCLEOSIDE TRIPHOSPHATES (dNTPs)

dTTP     dCTP     dATP     dGTP

2',3'-DIDEOXYRIBONUCLEOSIDE TRIPHOSPHATES (ddNTPs)

B=Thy
B=Cyt
B=Gua
B=Ade

3'-AMINO-2',3' DIDEOXYRIBONUCLEOSIDE TRIPHOSPHATES (3'-NH₂ ddNTPs)

B=Thy
B=Cyt
B=Gua
B=Ade

ARABINONUCLEOSIDE TRIPHOSPHATES (araNTPs)

B=Ura
B=Cyt

Ura=

METHODS FOR IDENTIFYING AND ISOLATING VARIANT T4 DNA POLYMERASES

This application is a divisional of Ser. No. 08/101,593 filed Aug. 2, 1993 now U.S. Pat. No. 5,547,859.

BACKGROUND OF THE INVENTION

The present invention relates to modifications of the DNA sequencing method developed by F. Sanger (Sanger, F., Nicklen, S., Coulson, A. R. (1977) *Proc. Natl. Acac. Sci. U.S.A.* 74, 5463–5467) as well as to novel enzymes which can be used for DNA sequencing. The Sanger sequencing method is based on in vitro DNA synthesis reactions in the presence of a primed DNA template, 2'-deoxyribonucleoside triphosphates (dNTPs, see FIG. 1), and 2',3'-dideoxyribonucleoside triphosphates (ddNTPs, FIG. 1). The latter, when incorporated by a DNA polymerase into a polynucleotide chain, terminate further chain elongation. The DNA products are thus a series of polynucleotide chains complementary to the template and terminated with specific dideoxynucleotides. The DNA sequencing products can be separated by size and the pattern of the products gives the DNA sequence.

In principle, DNA polymerases from a variety of organisms and a variety of chain-terminating nucleotides should be useful to sequence DNA. In practice, few DNA polymerases and chain-terminating nucleotides have been found to be suitable for this purpose. As an example of a DNA sequencing polymerase, the development of bacteriophage T7 DNA polymerase, Sequenace™, will be reviewed (Tabor, S., and Richardson, C. C. (1990) *J. Biol. Chem.* 265, 8322–8328). In order to obtain an unambiguous DNA sequence it is necessary that the majority of sequencing products terminate with a dideoxynucleotide and that all the sequencing products are represented equally. Two phage T7 DNA polymerase activities degrade DNA sequencing products and, thus, these activities must be eliminated in order to prevent degradation of dideoxynucleotide-terminated sequencing products. One activity, 3'→5' exonuclease activity, was removed by constructing an exonuclease deficient variant of T7 DNA polymerase. T7 DNA polymerase also has pyrophosphorolytic activity which can degrade the sequencing products. Pyrophosphatase was added to degrade pyrophosphate produced in the DNA sequencing reactions; without pyrophosphate, there is no pyrophosphorolysis. A further refinement of the sequencing reactions was to use $Mn^{2+}$ in place of $Mg^{2+}$ which resulted in a more equal distribution of reaction products. Although this brief review of the development of T7 DNA polymerase into a sequencing polymerase is a simplification, the review illustrates the point that modification of a natural DNA polymerase as well as development of reaction conditions is required in order to obtain high quality DNA sequence information using the chain-terminating sequencing method.

Optimal DNA sequencing conditions using the chain-terminating method have not yet been achieved. Ambiguous sequencing information is still observed which necessitates determining the DNA sequence of both DNA strands. Also, the use of $Mn^{2+}$ in place of $Mg^{2+}$ increases the amount of DNA template required for sequencing reactions. Thus it would be advantageous to develop novel methods that would improve or complement existing sequencing procedures.

The wild type T4 DNA polymerase gene has been cloned and the protein product expressed (Lin, T.-C., Rush, J. R., Spicer, E. K., and Konigsberg, W. H. (1987) *Proc. Natl. Acad. Sci. U.S.A.* 84, 7000–7004; U.S. Patent 4,935,361 to Lin et al.) and *E. coli* DNA polymerase II has been cloned and expressed (Bonner, C. A., Hays, S., McEntee, K., and Goodman, M. F. (1990) *Proc. Natl. Acad. Sci. U.S.A.* 87, 7663–7667). Standard oligonucleotide-directed mutagenesis techniques have been used to construct novel forms of T4 DNA polymerase and *E. coli* DNA polymerase II. Thus, the means exist to economically prepare large quantities of wild type and variant T4 DNA polymerase and *E. coli* DNA polymerase II.

Another aspect of the invention is to use genetic analysis to identify DNA polymerases with properties useful for DNA sequencing. T4 DNA polymerase is one of the most extensively genetically characterized DNA polymerases (Reha-Krantz, L. J. (1993) *In Molecular Biology of Bacteriophage* T4, ed. Karam J., American Association for Microbiology, in press); hence, some mutant DNA polymerases already identified may have properties useful for DNA sequencing and new mutants can be isolated directly. A method to isolate novel T4 DNA polymerases with useful DNA sequencing properties would be of additional utility.

SUMMARY OF THE INVENTION

In accordance with aspect of the invention, there are provided novel enzymes which may be used as DNA sequencing polymerases. These enzymes result from genetic mutations of family B DNA polymerases. These mutations eliminate the 3'→5' exonuclease activity of these novel family B DNA polymerases.

In accordance with another aspect of the invention, there are provided methods that enable phage T4 DNA polymerase and *E. coli* DNA polymerase II to be used as DNA sequencing polymerases. DNA polymerase modifications that convert phage T4 DNA polymerase and *E. coli* DNA polymerase II into DNA sequencing polymerases can also be used to similarly modify DNA polymerases having protein sequence homology with these two polymerases. DNA polymerases with protein sequence similarities to T4 DNA polymerase and *E. coli* DNA polymerase II include, but are not limited to, a group of DNA polymerases that are called Family B DNA polymerases (Braithwaite, D. K. and Ito, J. (1993) *Nucl. Acids Res.* 21, 787–802). Of particular relevance are the DNA polymerases from phages T2 and T6 which have extensive protein sequence homology to T4 DNA polymerase. Another extension of methods described here is that DNA polymerases with functional similarities to T4 DNA polymerase and *E. coli* DNA polymerase II may also be used to produce DNA sequence information with the chain-terminating nucleotides and methods disclosed hereinafter.

In accordance with another aspect of this invention there is provided a method to identify DNA polymerase modifications, having one or more specific amino acid substitutions in the polymerase protein sequence, that improve a given DNA polymerase in terms of DNA sequencing applications.

DETAILED DESCRIPTION OF THE INVENTION

Figure 1:
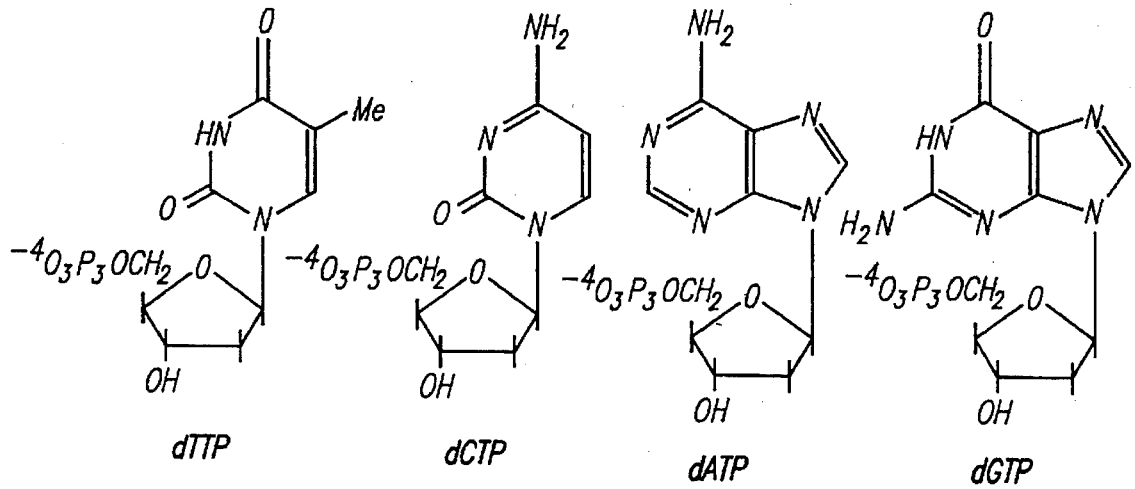
FIG. 1 depicts the structure of standard nucleotides and nucleotide analogs useful in the practice of the invention.
Figure 1:
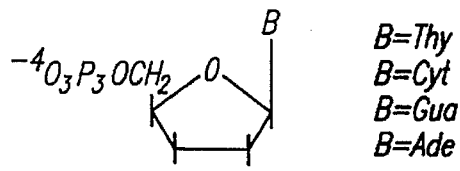
Figure 1:
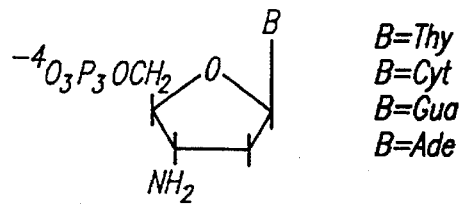
Figure 1:
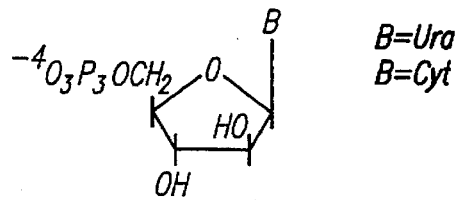
Figure 1:
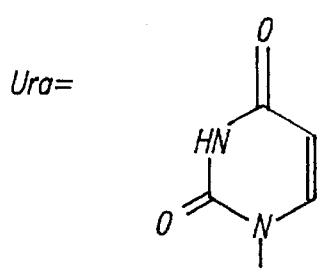

An aspect of the invention, namely to identify modified DNA polymerases with new properties that improve the ability of the modified DNA polymerases to carry out DNA sequencing reactions, is achieved by the design of a new genetic selection strategy that identifies modified DNA polymerases with superior DNA replication activities. The new genetic selection strategy has been designed around the T4 DNA polymerase.

T4 DNA polymerase (SEQ ID NO: 3 and 4) and *E. coli* DNA polymerase II (SEQ ID NO: 5 and 6), which have heretofore been unable to be used as sequencing polymerases, can be used as DNA sequencing polymerases in Sanger-type reactions if non-standard or novel combinations of chain-terminating nucleotides are used. Further to this discovery is the finding that inactivation of 3'→5' exonuclease activity in T4 DNA polymerase and *E. coli* DNA polymerase II improves the quality of the DNA sequence information obtained. In a further aspect, additional polymerase modifications have been discovered, which when combined with other modifications that reduce 3'→5' exonuclease activity, have the potential to produce a multiply modified DNA polymerase with advantageous DNA sequencing properties. Due to extensive sequence homology with T4 DNA polymerase, DNA polymerases such as phages T2 (SEQ ID NO: 1 and 2) and T6 DNA polymerases are particularly suitable in the application of the methods of the invention.

T4 DNA polymerase and *E. coli* DNA polymerase II can be used as effective DNA sequencing polymerases if the arabinonucleotides (FIG. 1), araUTP and araCTP, are used in place of the standard chain-terminating nucleotides ddTTP and ddCTP. The standard purine dideoxynucleotides (FIG. 1), ddATP and ddGTP, are effective chain-terminating nucleotides for T4 DNA polymerase and *E. coli* DNA polymerase II. DNA sequencing reactions for T4 DNA polymerase and *E. coli* DNA polymerase II differ from standard DNA sequencing reactions in that a novel combination of chain-terminating nucleotides is used. Although in principle any chain-terminating nucleotide may be used, DNA polymerases differ markedly in their ability to incorporate these nucleotides into the DNA chain. For T4 DNA polymerase and *E. coli* DNA polymerase II, the low incorporation of ddTTP and ddCTP by these enzymes have prevented the use of these standard chain-terminating nucleotides in sequencing protocols. The discovery alternative chain-terminating arabinonucleotides, araCTP and araUTP, can be incorporated relatively efficiently by T4 DNA polymerase and *E. coli* DNA polymerase II enables these DNA polymerases to be used as sequencing polymerases. The DNA sequencing method that uses reactions with the novel combinations of chain-terminating nucleotides—araCTP, araUTP, ddATP and ddGTP, is described, hereinbelow, in Method I.

A further discovery is that inactivation or significant reduction of the 3'→5' exonuclease activity of T4 DNA polymerase and *E. coli* DNA polymerase II enhances the quality of DNA sequence information obtained using the Method I sequencing reactions. T4 DNA polymerase 3'→5' exonuclease activity can be significantly reduced by an amino acid substitution including, but not limited to, one or more of the following amino acid substitutions in the enzyme: D112A +E114A, D219A and D324A. In the above nomenclature which is used herein throughout, the single letter code for amino acids is used. The numbers flanked by the single letter codes for amino acids are the codon numbers. For example, D112A+E114A indicates an alanine (A) substitution for aspartate (D) at codon position 112. D112A+ E114A indicates two amino acid substitutions in the modified DNA polymerase. To achieve these variants the following mutations were employed: for D112A the A nucleotide at position 335 is replaced with a C nucleotide thereby effecting a change of the D amino acid to an A amino acid, as is known to one of ordinary skill in the art other nucleotide changes are capable of effecting the same change; for E114A the A nucleotide at position 341 is replaced with a C nucleotide, as is known other nucleotide changes can effect the same amino acid change; for D219A the A and C nucleotides at position 656 and 657, respectively, are replaced with a C and a G nucleotide, respectively, as is known other nucleotide changes can effect the amino acid change; and for D324A the A nucleotide at position 971 is replaced with a C nucleotide, as is known other nucleotide changes can effect the same amino acid change. *E. coli* DNA polymerase II 3'→5' exonuclease activity can be significantly reduced by an amino acid substitution including, but not limited to, the following amino acid substitutions: D156A+E158A. To achieve these variants the following mutations were employed: for D156A the A nucleotide at position 467 is replaced with a C nucleotide, as is known other nucleotide changes can effect the same amino acid change; for E158A the A nucleotide at position 473 is replaced with a C nucleotide, as is known other nucleotide changes can effect the same amino acid change. Construction of 3'→5' exonuclease deficient variants of T4 DNA polymerase and *E. coli* DNA polymerase II is achieved by standard oligonucleotide mutagenesis procedures (for example, Kunkle, T. A., Roberts, J. D. and Zakour, R. A. (1987) *Method. Enz.* 154, 367–382).

Another aspect of the invention may be achieved by using chain-terminating nucleotides that are not used in standard DNA sequencing reactions. T4 DNA polymerase and *E. coli* DNA polymerase II may also be used as effective DNA sequencing polymerases if 3'amino-2',3'-dideoxyribonucleotides (3'-$NH_2$dNTPs) (FIG. 1) are used in place of the standard ddNTPs. This sequencing method is described herein below in Method II. Unmodified (wild type) T4 DNA polymerase and 3'→5' exonuclease deficient variants can be used in Method II reactions; the 3'→5' exonuclease deficient variant of *E. coli* DNA polymerase II has also been successfully used in Method II reactions.

The 3'→5' exonclease deficient form of T4 DNA polymerase can also be used to produce DNA sequence information without nucleotide analogs if the concentration of one of the four standard dNTPs is very low. For example, if the concentrations of dGTP, dCTP and dTTP are at 100 µM and the concentration of dATP is at 0.1 µM to 1 µM then sequencing products are observed that terminate one position before dATP is required for incorporation. With parallel reactions, each with one dNTP present at low concentration and the other three dNTPs present at high concentrations, the DNA sequence can be determined. This sequencing method is referred to hereinafter as Method III.

The third objective, namely to identify variant or modified DNA polymerases with new properties that enable the polymerases to have enhanced sequencing properties, has been achieved by designing a new strategy to select for novel DNA polymerases. The new strategy, a type of genetic selection, was developed for phage T4. The basic strategy begins with a phage T4 strain that has one or more mutations in the DNA polymerase gene which result in a variant (mutant) DNA polymerase which is partially defective in some aspect of DNA replication. Several types of DNA polymerase modifications can reduce the ability of DNA polymerase to replicate DNA efficiently. For example, alterations in the ability of the DNA polymerase to bind DNA template or dNTPs or in the ability of the DNA polymerase to translocate along the DNA template will reduce DNA replication efficiency. For phage T4, DNA polymerase mutants with reduced DNA replication activity can be readily identified. Phage T4 strains with mutant DNA polymerases that are partially defective in DNA replication cannot synthesize DNA if the bacterial host used in the infection contains the optA1 mutation. In other words, the *E.*

*coli* optA1 host restricts growth of T4 strains with mutant DNA polymerases defective in DNA replication activity. The basis of the restriction observed for the *E. coli* optA1 strain is that increased amounts of an enzyme that degrades dGTP is produced (Wurgler, S. S., and Richardson, C. C. (1990) *Proc. Natl. Acad. Sci. U.S.A.* 87, 2740–2744). Thus, phage T4 strains with variant DNA polymerases with reduced DNA replication activity cannot replicate DNA and produce phage progeny if the nucleotide pools, especially dGTP, are reduced.

In terms of development of a genetic selection strategy, conditions have been established which can be used to identify DNA replication defective DNA polymerases as well as to restrict production of progeny from phages with such defective DNA polymerases, namely the restricted production of phage progeny in infections of the *E. coli* optA1 bacterial host. These conditions, described hereinbelow, enable the selection of further modified (mutated) DNA polymerases with superior DNA replication ability. If the variant DNA polymerases with reduced DNA replication activity are further modified, for example by one or more additional amino acid substitutions, it may be that additional mutations/amino acid substitutions correct or compensate for the initial defect in DNA replication activity. Such further modified DNA polymerases will now be able to replicate DNA in the *E coli* optA1 host and phage progeny will be produced. Thus, detection of phage progeny on the *E. coli* optA1 host in infections with phage formerly restricted from producing progeny on this host allows for the selection of multiply mutant DNA polymerases that have the starting mutation (amino acid substitutions that decrease DNA replication activity) plus one or more new mutations that encode additional amino acid substitutions that correct or compensate for the starting DNA replication defect. The new correcting or compensating mutations (also called suppressor mutations in genetic terminology) can be identified by sequencing the phage DNA polymerase gene using standard procedures (McPheeters, D. S., Christensen, A., Young, E. T., Stormo, G., and Gold, L. (1986) Nucleic Acid Res. 14, 5813–5826; Reha-Krantz, L. J. (1988) J. Mol. Biol. 202, 711–724). The new mutations can be introduced into the phage T4 DNA polymerase gene or into T4 DNA polymerase expression vectors for further study. In contrast to the starting phage T4 DNA polymerases with reduced DNA replication ability, the new variant DNA polymerases have superior DNA replication ability because these variant DNA polymerases were selected on the basis of their ability to overcome, compensate or correct defects in variant DNA polymerase with reduced DNA replication activity. The genetic strategy to identify variant DNA polymerases with superior DNA replication abilities is highly sensitive as a single phage with the above described properties can be selected from a population of $10^8$ to $10^9$ phage.

Further to the invention, variant DNA polymerases with superior DNA replication activity have properties advantageous for DNA sequencing polymerase, such as enhanced primer extension which produces a more uniform distribution of sequencing products and enhanced DNA replication in template regions that may block or hinder replication by unmodified DNA polymerases. T4 DNA polymerase variants with superior DNA replication ability are predicted to improve the quality of DNA sequence information produced by Methods I, II, and III.

The genetic selection strategy described here for the detection of variant DNA polymerases with superior DNA replication ability can be applied to the DNA polymerases of other organisms it such defective DNA polymerases can be identified and if variants with correcting or compensating mutations can be selected.

DNA Sequencing Method I.

T4 DNA polymerase with significantly reduced 3'→5' exonuclease activity, such as variant forms with either D112A+E114A, D219A, or D324A amino acid substitutions, and *E. coli* DNA polymerase II with significantly reduced 3'→5' exonuclease activity, such as the variant form with D156A+E158A amino acid substitutions, can be used as DNA sequencing polymerases with the following set of chain-terminating nucleotides: ddATP, ddGTP, araCTP, and araUTP (FIG. 1).

Figure 2A:
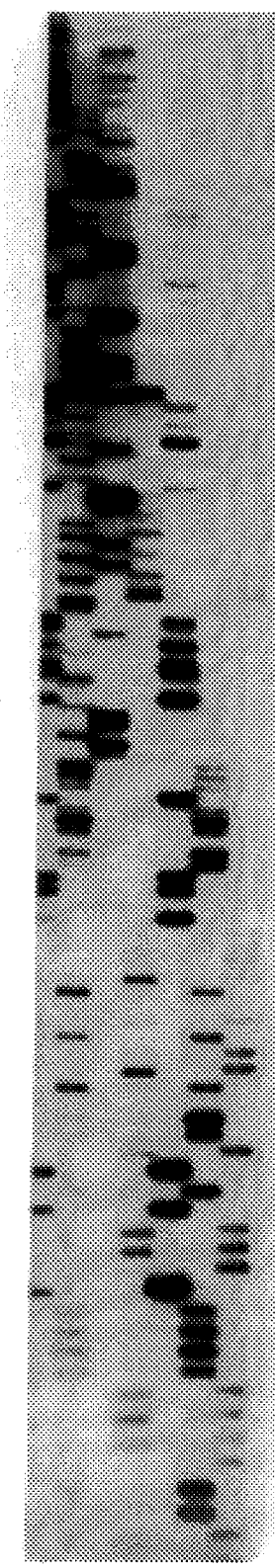
FIGS. 2A–C depicts DNA sequencing gels which resulted from the use of variant *E. coli* DNA polymerase II and T4 DNA polymerase.
Figure 2B:
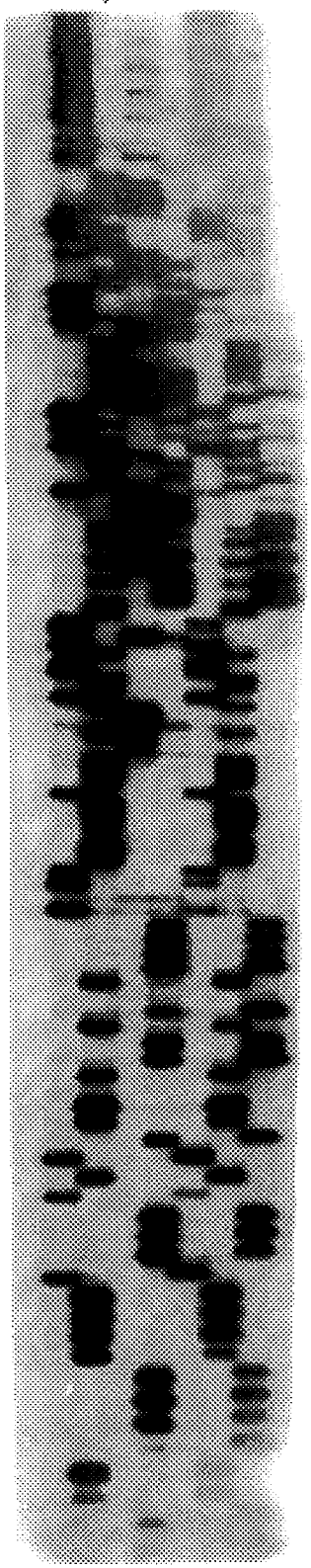
Figure 2C:
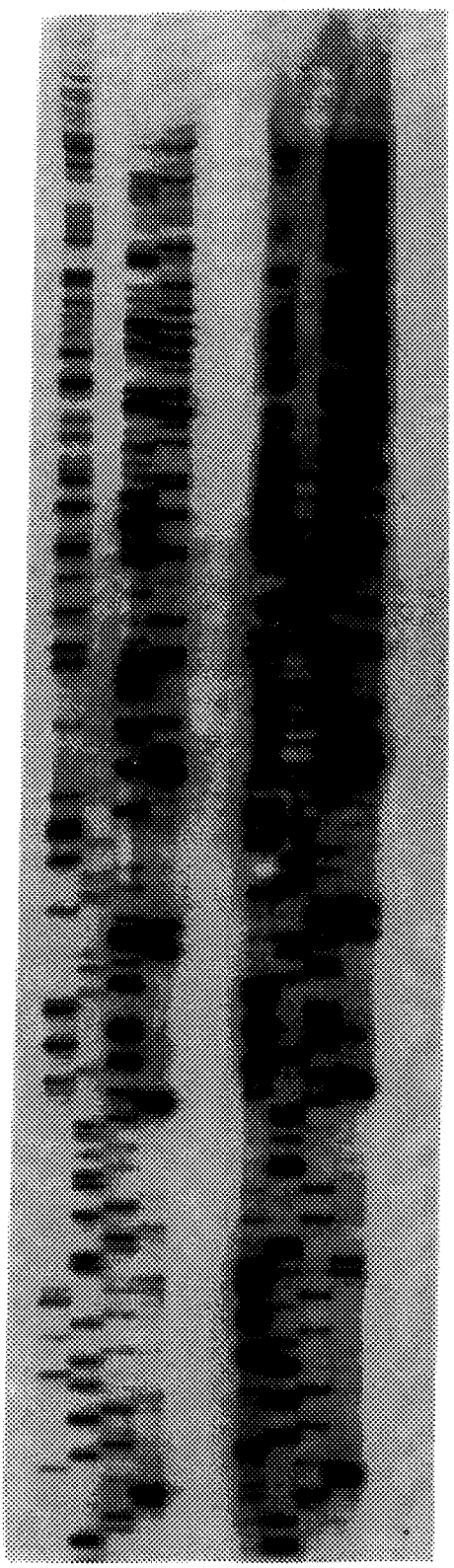

FIG. 2 shows photographs of three DNA sequencing gels. DNA sequencing patterns obtained with Method I are in panels A and B, lanes 1–4, and panel C. Panel A shows DNA sequencing reactions with the exonuclease deficient variant of *E. coli* DNA polymerase II. The reaction with ddGTP is in lane 1, the reaction with ddATP is in lane 2, the reaction with araCTP is in lane 3, and the reaction with araUTP is in lane 4. Panel B shows DNA sequencing reactions with the exonuclease deficient form of bacteriophage T4 DNA polymerase. Again, lane 1 has reactions with ddGTP, lane 2 has ddATP, lane 3 has araCTP, and lane 4 has araUTP. The reactions in panels A and B have $Mg^{2+}$ as the divalent metal cation. Sequencing patters are also obtained with $Mn^{2+}$ in place of $Mg^{2+}$. Method I reactions with $Mn^{2+}$ with the exonuclease deficient form of *E. coli* DNA polymerase II are shown on the left side of panel C, lanes 1–4; reactions with the exonuclease deficient form of T4 DNA polymerase are shown on the right side of panel C, lanes 1–4. Panel C, lanes 1–4 contain reactions with ddGTP (lane 1), ddATP (lane 2), araCTP (lane 3), and araUTP (lane 4).

DNA Sequencing Method II.

Wild type (unmodified) and 3'→5' exonuclease deficient forms of T4 DNA polymerase and the 3'→5' exonuclease deficient form of *E. coli* DNA polymerase II can be used as DNA sequencing polymerases with 3'amino-2', 3'-dideoxyribonucleotides (FIG. 1) as chain terminating nucleotides. Method II reactions for the exonuclease deficient form of *E. coli* DNA polymerase II are shown in FIG. 2, panel A, lanes 5–7. Lane five shows the reaction with 3'amino-2',3'-dideoxyGTP; lane 6 shows the reaction with 3'amino-2',3'-dideoxyATP; lane 7 shows the reaction with 3'amino-2',3-dideoxyTTP. Method II reactions for the exonuclease deficient form of T4 DNA polymerase are shown in panel B, lanes 5–7. Lane 5, 6 and 7 show reactions with 3'amino-2'3'dideoxyGTP, -ATP and -TTP, respectively.

The data demonstrate that the exonuclease deficient forms of *E. coli* DNA polymerase II and bacteriophage T4 DNA polymerases can produce DNA sequence information using a combination of the following chain-terminating nucleotides: ddGTP or 3'amino-2',3'-dideoxyGTP; ddATP or 3'amino-2',3'-dideoxyATP; araUTP or 3'amino-2',3'dideoxyTTP; and araCTP. In view of the good sequence patterns obtained with 3'amino-2'3'dideoxy-GTP, -ATP and -TTP, it is likely that 3'amino-2',3'-dideoxy-CTP will also be an effective chain-terminating nucleotide. No attempt was made to optimize conditions for Methods I or II in order to achieve equal band intensities or to increase the length of readable sequence for the reactions shown in FIG. 2. Nevertheless, the sequencing methods can provide sequence information for at least 300 bases. The exonuclease deficient form of T4 DNA polymerase is not required for sequencing reactions with the 3'amino-2',3'-dideoxyribonucleoside triphosphates.

Sample Experimental conditions for Methods I and II (FIG. 2).

Labeling reaction.

5 μl exonuclease deficient DNA polymerase; 300–400 units/ml for T4 DNA polymerase or for *E. coli* DNA polymerase II. One unit T4 DNA polymerase catalyzes 10 nmol of dTMP incorporation into DNA in 30 min at 30° C. One unit of *E. coli* DNA polymerase II catalyzes the incorporation of 1 pmol of dTMP into DNA in 1 min at 37° C. Although the reaction is typically conducted at 37° C., the reaction may be conducted in a temperature range from about 35° C. to about 42° C.

15 µl primer-M13 DNA complex, 15 nM

15 µl labeling reaction solution: 2 µM dGTP, dCTP, dTTP; 1 µM [a$^{32}$P]dATP; 50 mM Tris-HCl (pH 8.5); 5 mM MgCl$_2$ or 6 mM MnCl$_2$ for *E. coli* DNA polymerase II; 5 mM MgCl$_2$ or 0.5 mM MnCl$_2$ for T4 DNA polymerase; 5 mM dithiothreitol; 50 µg/ml bovine serum albumin.

The reaction mixtures were incubated 5 min at 37° C.

The primer may also be labeled at the 5'-end, or by including a labeled nucleotide in the extension reaction and by other standard methods.

Extension reaction.

4 µl labeling reaction mixture (from above)

4 µl termination solution: 50 µM dGTP, dATP, dCTP and dTTP; and one of the termination analogs listed below:

Method I: ddGTP, 1.6 mM; ddATP, 0.7 mM; araCTP, 0.5 mM; araUTP, 0.5 mM.

Method II: 3'-amino-2',3'-dideoxyGTP, 0.5 mM; 3'-amino-2',3'-dideoxyATP, 0 5 mM; 3'-amino-2',3'-dideoxyTTP, 0.5 mM Reactions were incubated at 5 min at 37° C. Reactions were stopped by adding formamide/EDTA.

Figure 3:
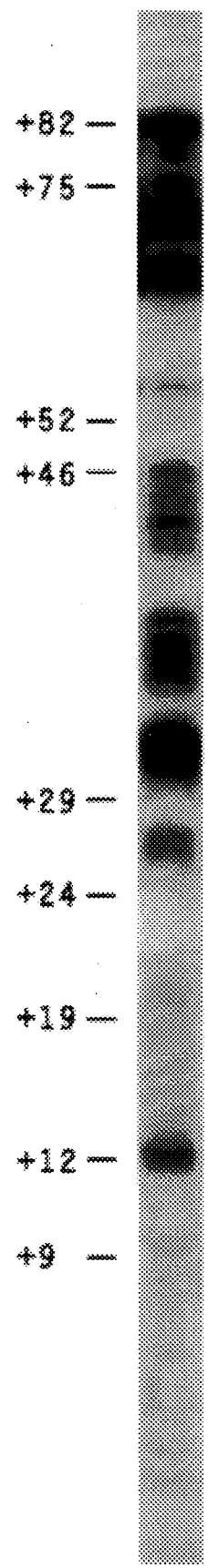
FIG. 3 depicts a DNA sequencing gel in which dATP is used at very low concentrations compared to the other standard nucleotides.

DNA sequencing Method III (FIG. 3).

Exonuclease deficient T4 DNA polymerase can produce DNA sequence information in reactions where one dNTP is at a low concentration (for example, 0.1 µM to 1 µM) and the other three dNTPs are at high concentrations (100 µM) (FIG. 3). DNA sequencing patterns are produced as with sequencing reactions with nucleotide analogs except that sequencing products produced by this method terminate one position before the dNTP at low concentrations is required.

Sample Experimental conditions:

25 mM Hepes (pH 7.5)

60 mM NaOAc 1 mM dithiothreitol

100 µM dGTP, dCTP and dTTP 0.1 µM dATP (1 µM dATP for longer DNA products)

0.2 mg/ml bovine serum albumin 7.5 nM 5'[$^{32}$P]labeled primer-template (expressed as the concentration of 3'-primer termini)

30 nM exonuclease deficient T4 DNA polymerase 6 mM Mg(OAc)$_2$

The reaction shown in FIG. 3 contained 0.1 µM dATP and was incubated for 1 min at 30° C. Conditions have not been optimized to obtain high amounts of sequence information; however, reactions in which the low concentration dNTP is at 1 µM yield sequence information greater than 100 bases.

Isolation of Novel T4 DNA Polymerases with Properties Advantageous for DNA Sequencing.

The first step in this aspect of the invention is to identify T4 strains with variant (mutant) DNA polymerases defective in some aspect of DNA replication. T4 strains with mutant DNA polymerase that have the amino acid substitutions listed below were chosen, but the genetic selection strategy is not limited to these mutants as any mutant DNA polymerase with defective DNA replication ability can be used. Variant (mutant) T4 DNA polymerases that are partially defective in some aspect of DNA replication cannot replicate DNA in the *E. coli* optA1 host.

T4 strains with mutant DNA polymerases with amino acid substitutions W213S, I417V, A737V or A777V cannot replicate DNA in the *E. coli* optA1 host. To achieve these variants the following mutations were employed: for W213S the G nucleotide at position 638 is replaced with a C nucleotide; for I417V the A nucleotide at position 1249 is replaced with a G nucleotide; for A737V the C nucleotide at position 2210 is replaced with a T nucleotide; and for A777V the C nucleotide at position 2330 is replaced with a T nucleotide. As is known other nucleotide replacements can cause the same amino acid changes.

The second step is to select T4 strains that can replicate DNA in the *E. coli* optA1 host even though the DNA polymerase still retains the amino acid substitution that alone reduces DNA replication ability and prevents replication of DNA in *E. coli* optA1 host. T4 strains that have acquired a second DNA polymerase mutation (or multiple mutations), either by spontaneous mutation or by mutagenesis treatment, that encodes a new amino acid substitution that can correct or compensate the DNA replication defect produced by the first amino acid substitution, will be able to replicate DNA in the *E. coli* optA1 host and produce phage progeny. DNA polymerases thus identified have at least two amino acid substitutions: the starting amino acid substitution and one or more new amino acid substitutions that restore DNA replication activity. This genetic selection strategy is of high sensitivity. A phage with a mutant DNA polymerase containing the starting amino acid substitution and the amino acid substitution(s) that restores DNA replication activity can be selected from a population of $10^8$ to $10^9$ phage.

The third step is to identify the DNA replication restoring mutation(s). This step utilizes standard sequencing procedures to find the new mutation(s) in the T4 DNA polymerase gene. Once the new mutation(s) has been identified, the mutation can be introduced into phage or into T4 DNA polymerase expression vectors using standard procedures. Unlike the starting, DNA replication defective DNA polymerase, the DNA polymerases with the correcting or compensating amino acid substitutions have superior DNA replication activity. A sample of the amino acid substitutions discovered using the genetic selection strategy described above include but are not limited to: I50L, G82D, G255S and E743K. To achieve these variants the following mutations were employed: for I50L the A nucleotide at position 148 is replaced with a C nucleotide; for G82D the G nucleotide at position 245 is replaced with an A nucleotide; for G255S the G nucleotide at position 763 is replaced with an A nucleotide; and for E743K the G nucleotide at position 2227 is replaced with, an A nucleotide. As is known other nucleotide replacements can effect the same amino acid changes.

Variant (mutant, modified) T4 DNA polymerases with amino acid substitutions that confer enhanced DNA replication activity have new properties advantageous for DNA sequencing. One frequent DNA sequencing problem is that DNA polymerases used in sequencing reactions pause or disassociate at some template sites. As a consequence of this premature stop in chain elongation, sequencing products are produced that are not terminated by a chain-terminating nucleotide. Another problem is that DNA polymerase incorporation of nucleotides and chain-terminating nucleotides is affected by the template sequence which may lead to an unequal distribution of sequencing products. Novel DNA polymerases with enhanced DNA replication activity may surmount these problems. The G82D-T4 DNA polymerase (also known as T4 mel 62 DNA polymerase) has been tested in primer extension assays and this novel DNA polymerase has been found to extend primers that are problematic for the wild type T4 DNA polymerase. An example of G82D-T4 DNA polymerase synthesis is given in FIG. 4.

Figure 4:
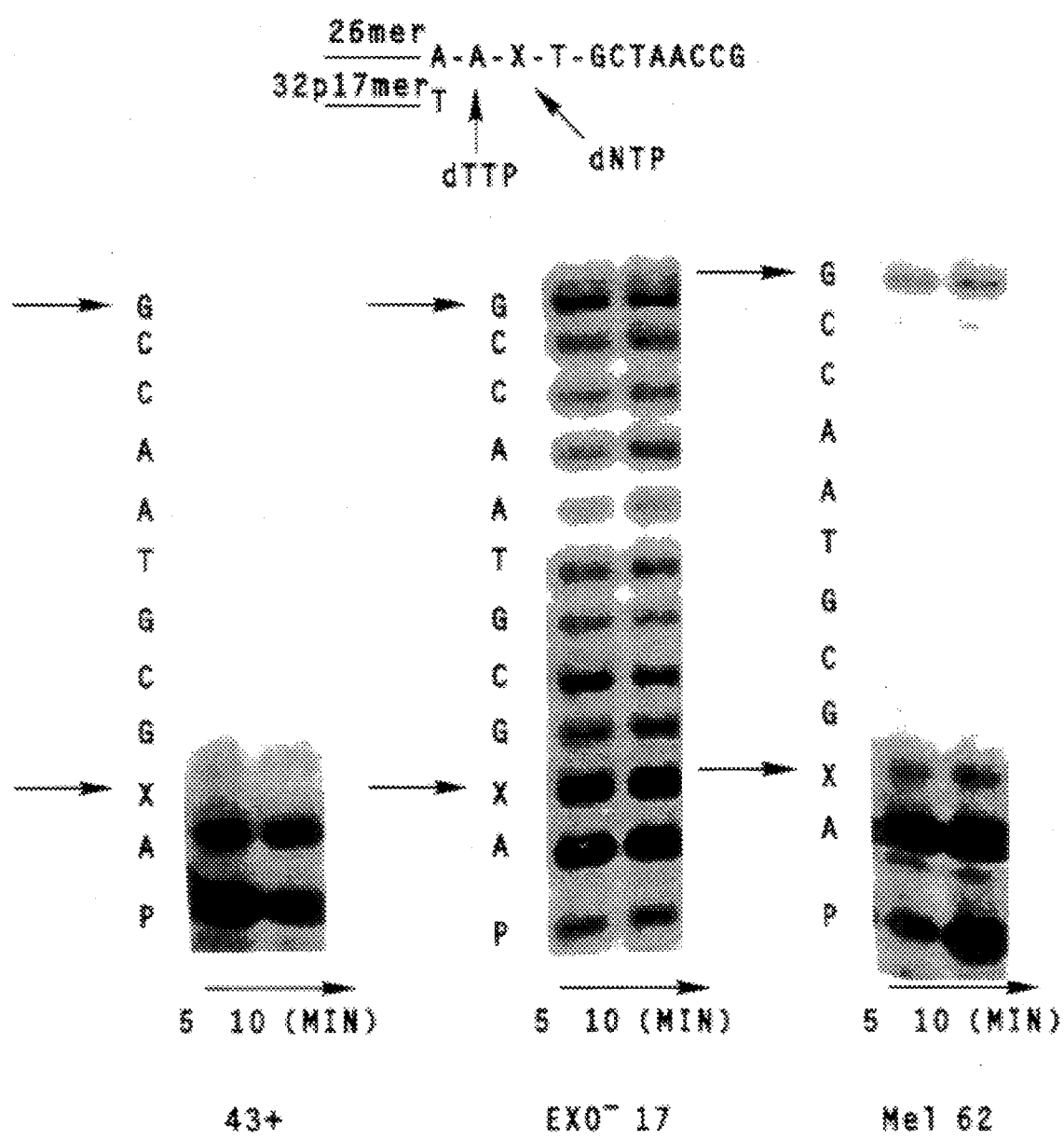
FIG. 4 depicts primer extension past a template abasic site (X) by wild-type and mutant T4 DNA polymerases.

FIG. 4 depicts the use of three T4 polymerases to copy a DNA template lesion (an abasic lesion—a base is missing on the template strand, indicated by X). The wild-type T4 polymerase has difficulty incorporating a nucleotide opposite X, as shown by the very light bands. A 3'-exonuclease deficient T4 polymerase mutant, EXO$^-$17, is able to incorporate nucleotides opposite X (note the intense band at X) and continue synthesis beyond the lesion. The T4 mel 62 polymerase is a mutant enzyme (it conveys a mutator phenotype in vivo) that has apparent normal (wild-type) levels of 3'-exonuclease and polymerase activities. It nevertheless is also able to incorporate nucleotides opposite X and to continue synthesis beyond X. What is most interesting is that the absence of "pausing" bands beyond X suggests that the mel 62 DNA polymerase remains bound to the primer template DNA more tightly than either EXO⁻17 or the wild-type polymerases. Thus, it is possible that this enzyme may be able to overcome template and substrate obstacles to synthesize long stretches of DNA.

It is contemplated that one or more amino acid substitutions that confer superior DNA replication activity will be combined with one or more amino acid substitutions that significantly reduce 3'→5' exonuclease activity to create a multiply modified novel T4 DNA polymerase with several properties that are advantageous for DNA sequencing polymerases.

It is known that polymerases, such as bacteriophage T7 DNA polymerase, may be used in conjunction with their accessory proteins thereby increasing the processivity of the polymerase by decreasing the rate of disassociation of the polymerase from the DNA strand to be sequenced.

In the case of the T4 polymerase, its accessory proteins, include but are not limited to, the following T4 gene products: gene product 32, 41, 45 and the 44/62 complex. In the case of E. coli DNA polymerase II, the accessory proteins are the following: β protein; the γ protein complex wherein the γ complex is composed of γ, δ, δ', χ, ψ; and SSB (single stranded binding protein) (note that β protein and γ complex are E. coli pol III accessory proteins). Use of these accessory proteins enhances the efficiency of the polymerases in sequencing DNA.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

We claim:

1. A method of identifying and isolating variant T4 DNA polymerases comprising the steps of:

identifying T4 strains having variant T4 DNA polymerases defective in some aspect of DNA replication;

isolating further mutated forms of said variant T4 DNA polymerases by selection in an *E. coli* optA1 host;

isolating T4 strains which contain variant T4 DNA polymerases having at least one additional mutation which corrects or compensates said defect in DNA replication;

identifying additional correcting/compensating mutation(s) in said variant T4 DNA polymerases; and introducing said identified correcting/compensating mutation(s) T4 DNA polymerases into T4 phage or T4 DNA polymerase expression vectors.

* * * * *

UNITED STATES PATENT AND TRADEMARK OFFICE
CERTIFICATE OF CORRECTION

PATENT NO. : 5,660,980       Page 1 of 2
DATED     : August 26, 1997
INVENTOR(S) : Myron F. Goodman, Linda J. Reha-Krantz It is certified that error appears in the above-identified patent and that said Letters Patent is hereby corrected as shown below:

| Column | Line | |
|---|---|---|
| 1 | 1 | change "METHODS", to --METHOD--. |
| 1 | 12 | change "*Acac.*", to --*Acad.*--. |
| 1 | 15 | change "in vitro", to --*in vitro*--. |
| 2 | 20 | after "with", insert --an--. |
| 3 | 41 | after "discovery", insert --that--. |
| 4 | 7 | after "effect the", insert --same--. |
| 4 | 65 | change "optA1", to --*optA1*--. |
| 5 | 1 | change "optA1", to --*optA1*--. |
| 5 | 3 | change "optA1", to --*optA1*--. |
| 5 | 17 | change "optA1", to --*optA1*--. |
| 5 | 25 | change "optA1", to --*optA1*--. |
| 5 | 27 | change "optA1", to --*optA1*--. |
| 5 | 38 | change "Nucleic Acid", to --*Nucleic Acid*--. |
| 5 | 39 | change "Res.", to --*Res.*--. |
|   |    | change "J. Mol. Biol.", to --*J. Mol. Biol.*--. |
| 5 | 65 | change "it", to --if--. |
| 6 | 4 | change "D112A+E114A", to --D112A + E114A--. |
| 6 | 7 | change "D156A+E158A", to --D156A + E158A--. |
| 6 | 21 | change "patters", to --patterns--. |
| 6 | 37 | change "five", to --5--. |
| 6 | 39 | change "3'-amino-2',3-dideoxyTTP", to --3'-amino-2',3'-dideoxyTTP--. |
| 7 | 2 | after the second occurrence of "C", delete the period |

UNITED STATES PATENT AND TRADEMARK OFFICE
CERTIFICATE OF CORRECTION

PATENT NO. : 5,660,980
DATED : August 26, 1997
INVENTOR(S) : Myron F. Goodman, Linda J. Reha-Krantz It is certified that error appears in the above-identified patent and that said Letters Patent is hereby corrected as shown below:

| Column | Line | |
|---|---|---|
| 7 | 4 | after the first occurrence of "C", delete the period |
| 7 | 7 | delete "[a$^{32}$P]", insert --[α$^{32}$P]--. |
| 7 | 21 | delete "0 5", insert --0.5--. |
| 7 | 33 | delete "before", insert --<u>before</u>--. |
| 7 | 61 | change "optA1", to --*optA1*--. |
| 7 | 64 | change "optA1", to --*optA1*--. |
| 8 | 6 | change "optA1", to --*optA1*--. |
| 8 | 9 | change "optA1", to --*optA1*--. |
| 8 | 15 | change "optA1", to --*optA1*--. |
| 8 | 41 | after "with", delete the comma. |
| 9 | 4 | change "in vivo", to --*in vivo*--. |
| 15-16 | | change amino acid 870 from "Lyy", to --Lys--. |
| 19-20 | | change amino acid 600 from "Gla", to --Glu--. |

Signed and Sealed this

Seventh Day of December, 1999

Q. TODD DICKINSON

*Attesting Officer*    Acting Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2694 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( a ) NAME/KEY: CDS
        ( B ) LOCATION: 1..2694

( x i ) SEQUENCE DESCRIPTION: SEQ ID NO:1:

```
ATG  AAA  GAA  TTT  TAT  ATC  TCT  ATC  GAA  ACA  GTC  GGA  AAT  AAT  ATT    45
Met  Lys  Glu  Phe  Tyr  Ile  Ser  Ile  Glu  Thr  Val  Gly  Asn  Asn  Ile
               5                         10                        15

ATT  GAA  CGT  TAT  ATT  GAT  GAA  AAC  GGA  AAG  GAA  CGT  ACT  CGT  GAA    90
Ile  Glu  Arg  Tyr  Ile  Asp  Glu  Asn  Gly  Lys  Glu  Arg  Thr  Arg  Glu
               20                        25                        30

GTA  GAA  TAT  CTT  CCG  ACT  ATG  TTT  AGG  CAT  TGT  AAG  GAA  GAG  TCA   135
Val  Glu  Tyr  Leu  Pro  Thr  Met  Phe  Arg  His  Cys  Lys  Glu  Glu  Ser
                    35                        40                   45

AAA  TAC  AAA  GAC  ATC  TAT  GGT  AAA  AAC  TGT  GCT  CCT  CAA  AAA  TTT   180
Lys  Tyr  Lys  Asp  Ile  Tyr  Gly  Lys  Asn  Cys  Ala  Pro  Gln  Lys  Phe
                    50                        55                   60

CCA  TCA  ATG  AAA  GAT  GCT  CGA  GAT  TGG  ATG  AAG  CGA  ATG  GAA  GAC   225
Pro  Ser  Met  Lys  Asp  Ala  Arg  Asp  Trp  Met  Lys  Arg  Met  Glu  Asp
                         65                        70                   75

ATC  GGT  CTC  GAA  GCT  CTC  GGT  ATG  AAC  GAT  TTT  AAA  CTC  GCT  TAT   270
Ile  Gly  Leu  Glu  Ala  Leu  Gly  Met  Asn  Asp  Phe  Lys  Leu  Ala  Tyr
                         80                        85                   90

ATC  AGT  GAT  ACG  TAT  GGT  TCA  GAA  ATT  GTT  TAT  GAC  CGA  AAA  TTT   315
Ile  Ser  Asp  Thr  Tyr  Gly  Ser  Glu  Ile  Val  Tyr  Asp  Arg  Lys  Phe
                         95                       100                  105

GTT  CGT  GTA  GCT  AAC  TGT  GAC  ATT  GAG  GTT  ACT  GGT  GAT  AAA  TTT   360
```

| | | | | | | | | | | | | | | |
|---|---|---|---|---|---|---|---|---|---|---|---|---|---|---|
| Val | Arg | Val | Ala | Asn<br>110 | Cys | Asp | Ile | Glu | Val<br>115 | Thr | Gly | Asp | Lys | Phe<br>120 |
| CCT | GAC | CCA | ATG | AAA | GCA | GAA | TAT | GAA | ATT | GAT | GCT | ATC | ACT | CAT | 405 |
| Pro | Asp | Pro | Met | Lys<br>125 | Ala | Glu | Tyr | Glu | Ile<br>130 | Asp | Ala | Ile | Thr | His<br>135 |
| TAT | GAT | TCA | ATT | GAC | GAC | CGT | TTT | TAT | GTT | TTC | GAC | CTT | TTG | AAT | 450 |
| Tyr | Asp | Ser | Ile | Asp<br>140 | Asp | Arg | Phe | Tyr | Val<br>145 | Phe | Asp | Leu | Leu | Asn<br>150 |
| TCA | ATG | TAC | GGT | TCA | GTA | TCA | AAA | TGG | GAT | GCA | AAG | TTA | GCT | GCT | 495 |
| Ser | Met | Tyr | Gly | Ser<br>155 | Val | Ser | Lys | Trp | Asp<br>160 | Ala | Lys | Leu | Ala | Ala<br>165 |
| AAG | CTT | GAC | TGT | GAA | GGT | GGT | GAT | GAA | GTT | CCT | CAA | GAA | ATT | CTT | 540 |
| Lys | Leu | Asp | Cys | Glu<br>170 | Gly | Gly | Asp | Glu | Val<br>175 | Pro | Gln | Glu | Ile | Leu<br>180 |
| GAC | CGA | GTA | ATT | TAT | ATG | CCA | TTT | GAT | AAT | GAG | CGT | GAT | ATG | CTC | 585 |
| Asp | Arg | Val | Ile | Tyr<br>185 | Met | Pro | Phe | Asp | Asn<br>190 | Glu | Arg | Asp | Met | Leu<br>195 |
| ATG | GAA | TAT | ATT | AAT | CTC | TGG | GAA | CAG | AAA | CGA | CCT | GCT | ATT | TTT | 630 |
| Met | Glu | Tyr | Ile | Asn<br>200 | Leu | Trp | Glu | Gln | Lys<br>205 | Arg | Pro | Ala | Ile | Phe<br>210 |
| ACT | GGT | TGG | AAT | ATT | GAG | GGG | TTT | GAC | GTT | CCG | TAT | ATC | ATG | AAT | 675 |
| Thr | Gly | Trp | Asn | Ile<br>215 | Glu | Gly | Phe | Asp | Val<br>220 | Pro | Tyr | Ile | Met | Asn<br>225 |
| CGC | GTT | AAA | ATG | ATT | CTG | GGT | GAA | CGC | AGT | ATG | AAA | CGT | TTC | TCT | 720 |
| Arg | Val | Lys | Met | Ile<br>230 | Leu | Gly | Glu | Arg | Ser<br>235 | Met | Lys | Arg | Phe | Ser<br>240 |
| CCA | ATC | GGT | CGG | GTA | AAA | TCT | AAA | CTA | ATT | CAA | AAT | ATG | TAC | GGT | 765 |
| Pro | Ile | Gly | Arg | Val<br>245 | Lys | Ser | Lys | Leu | Ile<br>250 | Gln | Asn | Met | Tyr | Gly<br>255 |
| AGC | AAA | GAA | ATT | TAT | TCT | ATT | GAT | GGC | GTA | TCT | ATT | CTT | GAT | TAT | 810 |
| Ser | Lys | Glu | Ile | Tyr<br>260 | Ser | Ile | Asp | Gly | Val<br>265 | Ser | Ile | Leu | Asp | Tyr<br>270 |
| TTA | GAT | TTG | TAC | AAG | AAA | TTC | GCT | TTT | ACT | AAT | TTG | CCG | TCA | TTC | 855 |
| Leu | Asp | Leu | Tyr | Lys<br>275 | Lys | Phe | Ala | Phe | Thr<br>280 | Asn | Leu | Pro | Ser | Phe<br>285 |
| TCT | TTG | GAA | TCA | GTT | GCT | CAA | CAT | GAA | ACC | AAA | AAA | GGT | AAA | TTA | 900 |
| Ser | Leu | Glu | Ser | Val<br>290 | Ala | Gln | His | Glu | Thr<br>295 | Lys | Lys | Gly | Lys | Leu<br>300 |
| CCA | TAC | GAC | GGT | CCT | ATT | AAT | AAA | CTT | CGT | GAG | ACT | AAT | CAT | CAA | 945 |
| Pro | Tyr | Asp | Gly | Pro<br>305 | Ile | Asn | Lys | Leu | Arg<br>310 | Glu | Thr | Asn | His | Gln<br>315 |
| CGA | TAC | ATT | AGT | TAT | AAC | ATC | ATT | GAC | GTA | GAA | TCA | GTT | CAA | GCA | 990 |
| Arg | Tyr | Ile | Ser | Tyr<br>320 | Asn | Ile | Ile | Asp | Val<br>325 | Glu | Ser | Val | Gln | Ala<br>330 |
| ATT | GAT | AAA | ATT | CGT | GGG | TTT | ATC | GAT | CTA | GTT | TTA | AGT | ATG | TCT | 1035 |
| Ile | Asp | Lys | Ile | Arg<br>335 | Gly | Phe | Ile | Asp | Leu<br>340 | Val | Leu | Ser | Met | Ser<br>345 |
| TAT | TAT | GCT | AAA | ATG | CCT | TTT | TCT | GGT | GTA | ATG | AGT | CCT | ATT | AAA | 1080 |
| Tyr | Tyr | Ala | Lys | Met<br>350 | Pro | Phe | Ser | Gly | Val<br>355 | Met | Ser | Pro | Ile | Lys<br>360 |
| ACT | TGG | GAT | GCT | ATT | ATT | TTT | AAC | TCA | TTG | AAA | GGT | GAA | CAC | AAG | 1125 |
| Thr | Trp | Asp | Ala | Ile<br>365 | Ile | Phe | Asn | Ser | Leu<br>370 | Lys | Gly | Glu | His | Lys<br>375 |
| GTT | ATT | CCT | CAA | CAA | GGT | TCG | CAC | GTT | AAA | CAG | AGT | TTT | CCG | GGT | 1170 |
| Val | Ile | Pro | Gln | Gln<br>380 | Gly | Ser | His | Val | Lys<br>385 | Gln | Ser | Phe | Pro | Gly<br>390 |
| GCA | TTT | GTA | TTT | GAA | CCT | AAA | CCA | ATT | GCT | CGT | CGA | TAC | ATT | ATG | 1215 |
| Ala | Phe | Val | Phe | Glu<br>395 | Pro | Lys | Pro | Ile | Ala<br>400 | Arg | Arg | Tyr | Ile | Met<br>405 |
| AGT | TTT | GAC | TTG | ACG | TCT | CTG | TAT | CCG | AGC | ATT | ATT | CGC | CAG | GTT | 1260 |

```
Ser Phe Asp Leu Thr Ser Leu Tyr Pro Ser Ile Ile Arg Gln Val
                410                 415                 420

AAC ATT AGT CCT GAA ACT ATT CGT GGT CAG TTT AAA GTT CAT CCA  1305
Asn Ile Ser Pro Glu Thr Ile Arg Gly Gln Phe Lys Val His Pro
                425                 430                 435

ATT CAT GAA TAT ATC GCA GGA ACA GCT CCT AAA CCA AGT GAT GAA  1350
Ile His Glu Tyr Ile Ala Gly Thr Ala Pro Lys Pro Ser Asp Glu
                440                 445                 450

TAT TCT TGT TCT CCG AAT GGA TGG ATG TAT GAT AAG CAT CAA GAA  1395
Tyr Ser Cys Ser Pro Asn Gly Trp Met Tyr Asp Lys His Gln Glu
                455                 460                 465

GGT ATC ATT CCA AAG GAA ATC GCT AAA GTA TTT TTC CAG CGT AAA  1440
Gly Ile Ile Pro Lys Glu Ile Ala Lys Val Phe Phe Gln Arg Lys
                470                 475                 480

GAT TGG AAA AAG AAA ATG TTC GCT GAA GAA ATG AAT GCC GAA GCT  1485
Asp Trp Lys Lys Lys Met Phe Ala Glu Glu Met Asn Ala Glu Ala
                485                 490                 495

ATT AAA AAG ATT ATT ATG AAA GGC GCA GGG TCT TGT TCA ACT AAA  1530
Ile Lys Lys Ile Ile Met Lys Gly Ala Gly Ser Cys Ser Thr Lys
                500                 505                 510

CCA GAA GTT GAA CGA TAT GTT AAG TTC ACT GAT GAT TTC TTA AAT  1575
Pro Glu Val Glu Arg Tyr Val Lys Phe Thr Asp Asp Phe Leu Asn
                515                 520                 525

GAA CTA TCG AAT TAT ACT GAA TCT GTT CTT AAT AGT CTG ATT GAA  1620
Glu Leu Ser Asn Tyr Thr Glu Ser Val Leu Asn Ser Leu Ile Glu
                530                 535                 540

GAA TGT GAA AAA GCA GCT ACA CTT GCT AAT ACA AAT CAG CTG AAC  1665
Glu Cys Glu Lys Ala Ala Thr Leu Ala Asn Thr Asn Gln Leu Asn
                545                 550                 555

CGT AAA ATT CTT ATT AAC AGT CTT TAT GGT GCT CTT GGT AAT ATT  1710
Arg Lys Ile Leu Ile Asn Ser Leu Tyr Gly Ala Leu Gly Asn Ile
                560                 565                 570

CAT TTC CGT TAC TAT GAT TTA CGA AAT GCT ACT GCT ATC ACA ATT  1755
His Phe Arg Tyr Tyr Asp Leu Arg Asn Ala Thr Ala Ile Thr Ile
                575                 580                 585

TTT GGT CAA GTT GGT ATT CAG TGG ATT GCT CGT AAA ATT AAT GAA  1800
Phe Gly Gln Val Gly Ile Gln Trp Ile Ala Arg Lys Ile Asn Glu
                590                 595                 600

TAT CTG AAT AAA GTA TGC GGA ACT AAT GAT GAA GAT TTC ATC GCA  1845
Tyr Leu Asn Lys Val Cys Gly Thr Asn Asp Glu Asp Phe Ile Ala
                605                 610                 615

GCA GGT GAT ACT GAT TCG GTA TAT GTT TGT GTA GAT AAA GTT ATT  1890
Ala Gly Asp Thr Asp Ser Val Tyr Val Cys Val Asp Lys Val Ile
                620                 625                 630

GAA AAA GTT GGT CTT GAC CGA TTC AAA GAG CAG AAC GAT TTG GTT  1935
Glu Lys Val Gly Leu Asp Arg Phe Lys Glu Gln Asn Asp Leu Val
                635                 640                 645

GAA TTC ATG AAT CAG TTT GGT AAG AAA AAG ATG GAA CCT ATG ATT  1980
Glu Phe Met Asn Gln Phe Gly Lys Lys Lys Met Glu Pro Met Ile
                650                 655                 660

GAT GTT GCA TAT CGT GAG TTA TGT GAT TAT ATG AAT AAC CGC GAG  2025
Asp Val Ala Tyr Arg Glu Leu Cys Asp Tyr Met Asn Asn Arg Glu
                665                 670                 675

CAT CTG ATG CAT ATG GAC CGT GAA GCT ATT TCT TGC CCT CCG CTT  2070
His Leu Met His Met Asp Arg Glu Ala Ile Ser Cys Pro Pro Leu
                680                 685                 690

GGT TCA AAG GGT GTT GGT GGA TTT TGG AAA GCG AAA AAA CGT TAT  2115
Gly Ser Lys Gly Val Gly Gly Phe Trp Lys Ala Lys Lys Arg Tyr
                695                 700                 705

GCT CTG AAC GTT TAT GAT ATG GAA GAT AAG CGA TTT GCT GAA CCG  2160
```

```
        Ala  Leu  Asn  Val  Tyr  Asp  Met  Glu  Asp  Lys  Arg  Phe  Ala  Glu  Pro
                            710                      715                      720

CAT  CTA  AAA  ATC  ATG  GGT  ATG  GAA  ACT  CAG  CAG  AGT  TCA  ACA  CCA   2205
        His  Leu  Lys  Ile  Met  Gly  Met  Glu  Thr  Gln  Gln  Ser  Ser  Thr  Pro
                            725                      730                      735

AAA  GCA  GTG  CAA  GAA  GCA  CTC  GAA  GAA  AGT  ATT  CGT  CGT  ATT  CTT   2250
        Lys  Ala  Val  Gln  Glu  Ala  Leu  Glu  Glu  Ser  Ile  Arg  Arg  Ile  Leu
                            740                      745                      750

CAG  GAA  GGC  GAA  GAG  TCT  GTC  CAA  GAA  TAT  TAC  AAG  AAC  TTC  GAG   2295
        Gln  Glu  Gly  Glu  Glu  Ser  Val  Gln  Glu  Tyr  Tyr  Lys  Asn  Phe  Glu
                            755                      760                      765

AAA  GAA  TAT  CGT  CAA  CTT  GAC  TAT  AAA  GTT  ATT  GCT  GAA  GTA  AAA   2340
        Lys  Glu  Tyr  Arg  Gln  Leu  Asp  Tyr  Lys  Val  Ile  Ala  Glu  Val  Lys
                            770                      775                      780

ACT  GCG  AAC  GAT  ATA  GCG  AAA  TAT  GAT  GAT  AAA  GGT  TGG  CCA  GGA   2385
        Thr  Ala  Asn  Asp  Ile  Ala  Lys  Tyr  Asp  Asp  Lys  Gly  Trp  Pro  Gly
                            795                      790                      795

TTT  AAA  TGT  CCG  TTC  CAT  ATT  CGT  GGT  GTG  CTA  ACT  TAT  CGT  CGA   2430
        Phe  Lys  Cys  Pro  Phe  His  Ile  Arg  Gly  Val  Leu  Thr  Tyr  Arg  Arg
                            800                      805                      810

GCT  GTT  AGT  GGT  CTG  GGT  GTA  GCT  CCA  ATT  TTG  GAT  GGA  AAT  AAA   2475
        Ala  Val  Ser  Gly  Leu  Gly  Val  Ala  Pro  Ile  Leu  Asp  Gly  Asn  Lys
                            815                      820                      825

GTA  ATG  GTT  CTT  CCA  TTA  CGT  GAA  GGA  AAT  CCG  TTT  GGT  GAT  AAG   2520
        Val  Met  Val  Leu  Pro  Leu  Arg  Glu  Gly  Asn  Pro  Phe  Gly  Asp  Lys
                            830                      835                      840

TGC  ATT  GCT  TGG  CCA  TCG  GGT  ACA  GAA  CTT  CCA  AAA  GAA  ATT  CGT   2565
        Cys  Ile  Ala  Trp  Pro  Ser  Gly  Thr  Glu  Leu  Pro  Lys  Glu  Ile  Arg
                            845                      850                      855

TCT  GAT  GTA  CTA  TCT  TGG  ATT  GAC  TAC  TCA  ACT  TTG  TTC  CAA  AAA   2610
        Ser  Asp  Val  Leu  Ser  Trp  Ile  Asp  Tyr  Ser  Thr  Leu  Phe  Gln  Lyy
                            860                      865                      870

TCG  TTT  GTT  AAA  CCG  CTT  GCG  GGT  ATG  TGT  GAA  TCG  GCA  GGT  ATG   2655
        Ser  Phe  Val  Lys  Pro  Leu  Ala  Gly  Met  Cys  Glu  Ser  Ala  Gly  Met
                            875                      880                      885

GAC  TAT  GAG  GAA  AAA  GCT  TCG  TTA  GAC  TTC  CTG  TTT  GGC              2694
        Asp  Tyr  Glu  Glu  Lys  Ala  Ser  Leu  Asp  Phe  Leu  Phe  Gly
                            890                      895             898
```

( 2 ) INFORMATION FOR SEQ ID NO:2:

( i ) SEQUENCE CHARACTERISTICS:
        ( A ) LENGTH: 898 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
        Met  Lys  Glu  Phe  Tyr  Ile  Ser  Ile  Glu  Thr  Val  Gly  Asn  Asn  Ile
                             5                       10                       15

Ile  Glu  Arg  Tyr  Ile  Asp  Glu  Asn  Gly  Lys  Glu  Arg  Thr  Arg  Glu
                            20                       25                       30

Val  Glu  Tyr  Leu  Pro  Thr  Met  Phe  Arg  His  Cys  Lys  Glu  Glu  Ser
                            35                       40                       45

Lys  Tyr  Lys  Asp  Ile  Tyr  Gly  Lys  Asn  Cys  Ala  Pro  Gln  Lys  Phe
                            50                       55                       60

Pro  Ser  Met  Lys  Asp  Ala  Arg  Asp  Trp  Met  Lys  Arg  Met  Glu  Asp
                            65                       70                       75

Ile  Gly  Leu  Glu  Ala  Leu  Gly  Met  Asn  Asp  Phe  Lys  Leu  Ala  Tyr
                            80                       85                       90
```

-continued

| | | | | | | | | | | | | | | |
|---|---|---|---|---|---|---|---|---|---|---|---|---|---|---|
| Ile | Ser | Asp | Thr | Tyr 95 | Gly | Ser | Glu | Ile | Val 100 | Tyr | Asp | Arg | Lys | Phe 105 |
| Val | Arg | Val | Ala | Asn 110 | Cys | Asp | Ile | Glu | Val 115 | Thr | Gly | Asp | Lys | Phe 120 |
| Pro | Asp | Pro | Met | Lys 125 | Ala | Glu | Tyr | Glu | Ile 130 | Asp | Ala | Ile | Thr | His 135 |
| Tyr | Asp | Ser | Ile | Asp 140 | Asp | Arg | Phe | Tyr | Val 145 | Phe | Asp | Leu | Leu | Asn 150 |
| Ser | Met | Tyr | Gly | Ser 155 | Val | Ser | Lys | Trp | Asp 160 | Ala | Lys | Leu | Ala | Ala 165 |
| Lys | Leu | Asp | Cys | Glu 170 | Gly | Gly | Asp | Glu | Val 175 | Pro | Gln | Glu | Ile | Leu 180 |
| Asp | Arg | Val | Ile | Tyr 185 | Met | Pro | Phe | Asp | Asn 190 | Glu | Arg | Asp | Met | Leu 195 |
| Met | Glu | Tyr | Ile | Asn 200 | Leu | Trp | Glu | Gln | Lys 205 | Arg | Pro | Ala | Ile | Phe 210 |
| Thr | Gly | Trp | Asn | Ile 215 | Glu | Gly | Phe | Asp | Val 220 | Pro | Tyr | Ile | Met | Asn 225 |
| Arg | Val | Lys | Met | Ile 230 | Leu | Gly | Glu | Arg | Ser 235 | Met | Lys | Arg | Phe | Ser 240 |
| Pro | Ile | Gly | Arg | Val 245 | Lys | Ser | Lys | Leu | Ile 250 | Gln | Asn | Met | Tyr | Gly 255 |
| Ser | Lys | Glu | Ile | Tyr 260 | Ser | Ile | Asp | Gly | Val 265 | Ser | Ile | Leu | Asp | Tyr 270 |
| Leu | Asp | Leu | Tyr | Lys 275 | Lys | Phe | Ala | Phe | Thr 280 | Asn | Leu | Pro | Ser | Phe 285 |
| Ser | Leu | Glu | Ser | Val 290 | Ala | Gln | His | Glu | Thr 295 | Lys | Lys | Gly | Lys | Leu 300 |
| Pro | Tyr | Asp | Gly | Pro 305 | Ile | Asn | Lys | Leu | Arg 310 | Glu | Thr | Asn | His | Gln 315 |
| Arg | Tyr | Ile | Ser | Tyr 320 | Asn | Ile | Ile | Asp | Val 325 | Glu | Ser | Val | Gln | Ala 330 |
| Ile | Asp | Lys | Ile | Arg 335 | Gly | Phe | Ile | Asp | Leu 340 | Val | Leu | Ser | Met | Ser 345 |
| Tyr | Tyr | Ala | Lys | Met 350 | Pro | Phe | Ser | Gly | Val 355 | Met | Ser | Pro | Ile | Lys 360 |
| Thr | Trp | Asp | Ala | Ile 365 | Ile | Phe | Asn | Ser | Leu 370 | Lys | Gly | Glu | His | Lys 375 |
| Val | Ile | Pro | Gln | Gln 380 | Gly | Ser | His | Val | Lys 385 | Gln | Ser | Phe | Pro | Gly 390 |
| Ala | Phe | Val | Phe | Glu 395 | Pro | Lys | Pro | Ile | Ala 400 | Arg | Arg | Tyr | Ile | Met 405 |
| Ser | Phe | Asp | Leu | Thr 410 | Ser | Leu | Tyr | Pro | Ser 415 | Ile | Ile | Arg | Gln | Val 420 |
| Asn | Ile | Ser | Pro | Glu 425 | Thr | Ile | Arg | Gly | Gln 430 | Phe | Lys | Val | His | Pro 435 |
| Ile | His | Glu | Tyr | Ile 440 | Ala | Gly | Thr | Ala | Pro 445 | Lys | Pro | Ser | Asp | Glu 450 |
| Tyr | Ser | Cys | Ser | Pro 455 | Asn | Gly | Trp | Met | Tyr 460 | Asp | Lys | His | Gln | Glu 465 |
| Gly | Ile | Ile | Pro | Lys 470 | Glu | Ile | Ala | Lys | Val 475 | Phe | Phe | Gln | Arg | Lys 480 |
| Asp | Trp | Lys | Lys | Lys | Met | Phe | Ala | Glu | Glu | Met | Asn | Ala | Glu | Ala |

|     |     |     |     |     |     |     |     | 485 |     |     |     |     | 490 |     |     |     |     | 495 |     |
| --- | --- | --- | --- | --- | --- | --- | --- | --- | --- | --- | --- | --- | --- | --- | --- | --- | --- | --- | --- |
| Ile | Lys | Lys | Ile | Ile 500 | Met | Lys | Gly | Ala | Gly 505 | Ser | Cys | Ser | Thr | Lys 510 |
| Pro | Glu | Val | Glu | Arg 515 | Tyr | Val | Lys | Phe | Thr 520 | Asp | Asp | Phe | Leu | Asn 525 |
| Glu | Leu | Ser | Asn | Tyr 530 | Thr | Glu | Ser | Val | Leu 535 | Asn | Ser | Leu | Ile | Glu 540 |
| Glu | Cys | Glu | Lys | Ala 545 | Ala | Thr | Leu | Ala | Asn 550 | Thr | Asn | Gln | Leu | Asn 555 |
| Arg | Lys | Ile | Leu | Ile 560 | Asn | Ser | Leu | Tyr | Gly 565 | Ala | Leu | Gly | Asn | Ile 570 |
| His | Phe | Arg | Tyr | Tyr 575 | Asp | Leu | Arg | Asn | Ala 580 | Thr | Ala | Ile | Thr | Ilu 585 |
| Phe | Gly | Gln | Val | Gly 590 | Ile | Gln | Trp | Ile | Ala 595 | Arg | Lys | Ile | Asn | Gla 600 |
| Tyr | Leu | Asn | Lys | Val 605 | Cys | Gly | Thr | Asn | Asp 610 | Glu | Asp | Phe | Ile | Ale 615 |
| Ala | Gly | Asp | Thr | Asp 620 | Ser | Val | Tyr | Val | Cys 625 | Val | Asp | Lys | Val | Ile 630 |
| Glu | Lys | Val | Gly | Leu 635 | Asp | Arg | Phe | Lys | Glu 640 | Gln | Asn | Asp | Leu | Val 645 |
| Glu | Phe | Met | Asn | Gln 650 | Phe | Gly | Lys | Lys | Lys 655 | Met | Glu | Pro | Met | Ile 660 |
| Asp | Val | Ala | Tyr | Arg 665 | Glu | Leu | Cys | Asp | Tyr 670 | Met | Asn | Asn | Arg | Glu 675 |
| His | Leu | Met | His | Met 680 | Asp | Arg | Glu | Ala | Ile 685 | Ser | Cys | Pro | Pro | Leu 690 |
| Gly | Ser | Lys | Gly | Val 695 | Gly | Gly | Phe | Trp | Lys 700 | Ala | Lys | Lys | Arg | Tyr 705 |
| Ala | Leu | Asn | Val | Tyr 710 | Asp | Met | Glu | Asp | Lys 715 | Arg | Phe | Ala | Glu | Pro 720 |
| His | Leu | Lys | Ile | Met 725 | Gly | Met | Glu | Thr | Gln 730 | Gln | Ser | Ser | Thr | Pro 735 |
| Lys | Ala | Val | Gln | Glu 740 | Ala | Leu | Glu | Glu | Ser 745 | Ile | Arg | Arg | Ile | Leu 750 |
| Gln | Glu | Gly | Glu | Glu 755 | Ser | Val | Gln | Glu | Tyr 760 | Tyr | Lys | Asn | Phe | Glu 765 |
| Lys | Glu | Tyr | Arg | Gln 770 | Leu | Asp | Tyr | Lys | Val 775 | Ile | Ala | Glu | Val | Lys 780 |
| Thr | Ala | Asn | Asp | Ile 785 | Ala | Lys | Tyr | Asp | Asp 790 | Lys | Gly | Trp | Pro | Gly 795 |
| Phe | Lys | Cys | Pro | Phe 800 | His | Ile | Arg | Gly | Val 805 | Leu | Thr | Tyr | Arg | Arg 810 |
| Ala | Val | Ser | Gly | Leu 815 | Gly | Val | Ala | Pro | Ile 820 | Leu | Asp | Gly | Asn | Lys 825 |
| Val | Met | Val | Leu | Pro 830 | Leu | Arg | Glu | Gly | Asn 835 | Pro | Phe | Gly | Asp | Lys 840 |
| Cys | Ile | Ala | Trp | Pro 845 | Ser | Gly | Thr | Glu | Leu 850 | Pro | Lys | Glu | Ile | Arg 855 |
| Ser | Asp | Val | Leu | Ser 860 | Trp | Ile | Asp | Tyr | Ser 865 | Thr | Leu | Phe | Gln | Lys 870 |
| Ser | Phe | Val | Lys | Pro 875 | Leu | Ala | Gly | Met | Cys 880 | Glu | Ser | Ala | Gly | Met 885 |

| Asp | Tyr | Glu | Glu | Lys | Ala | Ser | Leu | Asp | Phe | Leu | Phe | Gly |
|---|---|---|---|---|---|---|---|---|---|---|---|---|
|   |   |   |   | 890 |   |   |   |   | 895 |   |   | 898 |

( 2 ) INFORMATION FOR SEQ ID NO:3:

( i ) SEQUENCE CHARACTERISTICS:
        ( A ) LENGTH: 2694 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( a ) NAME/KEY: CDS
        ( B ) LOCATION: 1..2694

( x i ) SEQUENCE DESCRIPTION: SEQ ID NO:3:

```
ATG  AAA  GAA  TTT  TAT  ATC  TCT  ATT  GAA  ACA  GTC  GGA  AAT  AAC  ATT    45
Met  Lys  Glu  Phe  Tyr  Ile  Ser  Ile  Glu  Thr  Val  Gly  Asn  Asn  Ile
               5                   10                          15

GTT  GAA  CGT  TAT  ATT  GAT  GAA  AAT  GGA  AAG  GAA  CGT  ACC  CGT  GAA    90
Val  Glu  Arg  Tyr  Ile  Asp  Glu  Asn  Gly  Lys  Glu  Arg  Thr  Arg  Glu
               20                  25                          30

GTA  GAA  TAT  CTT  CCA  ACT  ATG  TTT  AGG  CAT  TGT  AAG  GAA  GAG  TCA   135
Val  Glu  Tyr  Leu  Pro  Thr  Met  Phe  Arg  His  Cys  Lys  Glu  Glu  Ser
               35                  40                          45

AAA  TAC  AAA  GAC  ATC  TAT  GGT  AAA  AAC  TGC  GCT  CCT  CAA  AAA  TTT   180
Lys  Tyr  Lys  Asp  Ile  Tyr  Gly  Lys  Asn  Cys  Ala  Pro  Gln  Lys  Phe
               50                  55                          60

CCA  TCA  ATG  AAA  GAT  GCT  CGA  GAT  TGG  ATG  AAG  CGA  ATG  GAA  GAC   225
Pro  Ser  Met  Lys  Asp  Ala  Arg  Asp  Trp  Met  Lys  Arg  Met  Glu  Asp
               65                  70                          75

ATC  GGT  CTC  GAA  GCT  CTC  GGT  ATG  AAC  GAT  TTT  AAA  CTC  GCT  TAT   270
Ile  Gly  Leu  Glu  Ala  Leu  Gly  Met  Asn  Asp  Phe  Lys  Leu  Ala  Tyr
               80                  85                          90

ATA  AGT  GAT  ACA  TAT  GGT  TCA  GAA  ATT  GTT  TAT  GAC  CGA  AAA  TTT   315
Ile  Ser  Asp  Thr  Tyr  Gly  Ser  Glu  Ile  Val  Tyr  Asp  Arg  Lys  Phe
               95                  100                         105

GTT  CGT  GTA  GCT  AAC  TGT  GAC  ATT  GAG  GTT  ACT  GGT  GAT  AAA  TTT   360
Val  Arg  Val  Ala  Asn  Cys  Asp  Ile  Glu  Val  Thr  Gly  Asp  Lys  Phe
               110                 115                         120

CCT  GAC  CCA  ATG  AAA  GCA  GAA  TAT  GAA  ATT  GAT  GCT  ATC  ACT  CAT   405
Pro  Asp  Pro  Met  Lys  Ala  Glu  Tyr  Glu  Ile  Asp  Ala  Ile  Thr  His
               125                 130                         135

TAC  GAT  TCA  ATT  GAC  GAT  CGT  TTT  TAT  GTT  TTC  GAC  CTT  TTG  AAT   450
Tyr  Asp  Ser  Ile  Asp  Asp  Arg  Phe  Tyr  Val  Phe  Asp  Leu  Leu  Asn
               140                 145                         150

TCA  ATG  TAC  GGT  TCA  GTA  TCA  AAA  TGG  GAT  GCA  AAG  TTA  GCT  GCT   495
Ser  Met  Tyr  Gly  Ser  Val  Ser  Lys  Trp  Asp  Ala  Lys  Leu  Ala  Ala
               155                 160                         165

AAG  CTT  GAC  TGT  GAA  GGT  GGT  GAT  GAA  GTT  CCT  CAA  GAA  ATT  CTT   540
Lys  Leu  Asp  Cys  Glu  Gly  Gly  Asp  Glu  Val  Pro  Gln  Glu  Ile  Leu
               170                 175                         180

GAC  CGA  GTA  ATT  TAT  ATG  CCA  TTC  GAT  AAT  GAG  CGT  GAT  ATG  CTC   585
Asp  Arg  Val  Ile  Tyr  Met  Pro  Phe  Asp  Asn  Glu  Arg  Asp  Met  Leu
               185                 190                         195

ATG  GAA  TAT  ATC  AAT  CTT  TGG  GAA  CAG  AAA  CGA  CCT  GCT  ATT  TTT   630
Met  Glu  Tyr  Ile  Asn  Leu  Trp  Glu  Gln  Lys  Arg  Pro  Ala  Ile  Phe
               200                 205                         210

ACT  GGT  TGG  AAT  ATT  GAG  GGG  TTT  GAC  GTT  CCG  TAT  ATC  ATG  AAT   675
Thr  Gly  Trp  Asn  Ile  Glu  Gly  Phe  Asp  Val  Pro  Tyr  Ile  Met  Asn
               215                 220                         225
```

```
CGT GTT AAA ATG ATT CTG GGT GAA CGT AGT ATG AAA CGT TTC TCT   720
Arg Val Lys Met Ile Leu Gly Glu Arg Ser Met Lys Arg Phe Ser
            230             235             240

CCA ATC GGT CGG GTA AAA TCT AAA CTA ATT CAA AAT ATG TAC GGT   765
Pro Ile Gly Arg Val Lys Ser Lys Leu Ile Gln Asn Met Tyr Gly
            245             250             255

AGC AAA GAA ATT TAT TCT ATT GAT GGC GTA TCT ATT CTT GAT TAT   810
Ser Lys Glu Ile Tyr Ser Ile Asp Gly Val Ser Ile Leu Asp Tyr
            260             265             270

TTA GAT TTG TAC AAG AAA TTC GCT TTT ACT AAT TTG CCG TCA TTC   855
Leu Asp Leu Tyr Lys Lys Phe Ala Phe Thr Asn Leu Pro Ser Phe
            275             280             285

TCT TTG GAA TCA GTT GCT CAA CAT GAA ACC AAA AAA GGT AAA TTA   900
Ser Leu Glu Ser Val Ala Gln His Glu Thr Lys Lys Gly Lys Leu
            290             295             300

CCA TAC GAC GGT CCT ATT AAT AAA CTT CGT GAG ACT AAT CAT CAA   945
Pro Tyr Asp Gly Pro Ile Asn Lys Leu Arg Glu Thr Asn His Gln
            305             310             315

CGA TAC ATT AGT TAT AAC ATC ATT GAC GTA GAA TCA GTT CAA GCA   990
Arg Tyr Ile Ser Tyr Asn Ile Ile Asp Val Glu Ser Val Gln Ala
            320             325             330

ATC GAT AAA ATT CGT GGG TTT ATC GAT CTA GTT TTA AGT ATG TCT  1035
Ile Asp Lys Ile Arg Gly Phe Ile Asp Leu Val Leu Ser Met Ser
            335             340             345

TAT TAC GCT AAA ATG CCT TTT TCT GGT GTA ATG AGT CCT ATT AAA  1080
Tyr Tyr Ala Lys Met Pro Phe Ser Gly Val Met Ser Pro Ile Lys
            350             355             360

ACT TGG GAT GCT ATT ATT TTT AAC TCA TTG AAA GGT GAA CAT AAG  1125
Thr Trp Asp Ala Ile Ile Phe Asn Ser Leu Lys Gly Glu His Lys
            365             370             375

GTT ATT CCT CAA CAA GGT TCG CAC GTT AAA CAG AGT TTT CCG GGT  1170
Val Ile Pro Gln Gln Gly Ser His Val Lys Gln Ser Phe Pro Gly
            380             385             390

GCA TTT GTG TTT GAA CCT AAA CCA ATT GCA CGT CGA TAC ATT ATG  1215
Ala Phe Val Phe Glu Pro Lys Pro Ile Ala Arg Arg Tyr Ile Met
            395             400             405

AGT TTT GAC TTG ACG TCT CTG TAT CCG AGC ATT ATT CGC CAG GTT  1260
Ser Phe Asp Leu Thr Ser Leu Tyr Pro Ser Ile Ile Arg Gln Val
            410             415             420

AAC ATT AGT CCT GAA ACT ATT CGT GGT CAG TTT AAA GTT CAT CCA  1305
Asn Ile Ser Pro Glu Thr Ile Arg Gly Gln Phe Lys Val His Pro
            425             430             435

ATT CAT GAA TAT ATC GCA GGA ACA GCT CCT AAA CCG AGT GAT GAA  1350
Ile His Glu Tyr Ile Ala Gly Thr Ala Pro Lys Pro Ser Asp Glu
            440             445             450

TAT TCT TGT TCT CCG AAT GGA TGG ATG TAT GAT AAA CAT CAA GAA  1395
Tyr Ser Cys Ser Pro Asn Gly Trp Met Tyr Asp Lys His Gln Glu
            455             460             465

GGT ATC ATT CCA AAG GAA ATC GCT AAA GTA TTT TTC CAG CGT AAA  1440
Gly Ile Ile Pro Lys Glu Ile Ala Lys Val Phe Phe Gln Arg Lys
            470             475             480

GAC TGG AAA AAG AAA ATG TTC GCT GAA GAA ATG AAT GCC GAA GCT  1485
Asp Trp Lys Lys Lys Met Phe Ala Glu Glu Met Asn Ala Glu Ala
            485             490             495

ATT AAA AAG ATT ATT ATG AAA GGC GCA GGG TCT TGT TCA ACT AAA  1530
Ile Lys Lys Ile Ile Met Lys Gly Ala Gly Ser Cys Ser Thr Lys
            500             505             510

CCA GAA GTT GAA CGA TAT GTT AAG TTC AGT GAT GAT TTC TTA AAT  1575
Pro Glu Val Glu Arg Tyr Val Lys Phe Ser Asp Asp Phe Leu Asn
            515             520             525
```

```
GAA CTA TCG AAT TAC ACC GAA TCT GTT CTC AAT AGT CTG ATT GAA   1620
Glu Leu Ser Asn Tyr Thr Glu Ser Val Leu Asn Ser Leu Ile Glu
            530             535             540

GAA TGT GAA AAA GCA GCT ACA CTT GCT AAT ACA AAT CAG CTG AAC   1665
Glu Cys Glu Lys Ala Ala Thr Leu Ala Asn Thr Asn Gln Leu Asn
            545             550             555

CGT AAA ATT CTC ATT AAC AGT CTT TAT GGT GCT CTT GGT AAT ATT   1710
Arg Lys Ile Leu Ile Asn Ser Leu Tyr Gly Ala Leu Gly Asn Ile
            560             565             570

CAT TTC CGT TAC TAT GAT TTG CGA AAT GCT ACT GCT ATC ACA ATT   1755
His Phe Arg Tyr Tyr Asp Leu Arg Asn Ala Thr Ala Ile Thr Ile
            575             580             585

TTC GGC CAA GTC GGT ATT CAG TGG ATT GCT CGT AAA ATT AAT GAA   1800
Phe Gly Gln Val Gly Ile Gln Trp Ile Ala Arg Lys Ile Asn Glu
            590             595             600

TAT CTG AAT AAA GTA TGC GGA ACT AAT GAT GAA GAT TTC ATT GCA   1845
Tyr Leu Asn Lys Val Cys Gly Thr Asn Asp Glu Asp Phe Ile Ala
            605             610             615

GCA GGT GAT ACT GAT TCG GTA TAT GTT TGC GTA GAT AAA GTT ATT   1890
Ala Gly Asp Thr Asp Ser Val Tyr Val Cys Val Asp Lys Val Ile
            620             625             630

GAA AAA GTT GGT CTT GAC CGA TTC AAA GAG CAG AAC GAT TTG GTT   1935
Glu Lys Val Gly Leu Asp Arg Phe Lys Glu Gln Asn Asp Leu Val
            635             640             645

GAA TTC ATG AAT CAG TTC GGT AAG AAA AAG ATG GAA CCT ATG ATT   1980
Glu Phe Met Asn Gln Phe Gly Lys Lys Lys Met Glu Pro Met Ile
            650             655             660

GAT GTT GCA TAT CGT GAG TTA TGT GAT TAT ATG AAT AAC CGC GAG   2025
Asp Val Ala Tyr Arg Glu Leu Cys Asp Tyr Met Asn Asn Arg Glu
            665             670             675

CAT CTG ATG CAT ATG GAC CGT GAA GCT ATT TCT TGC CCT CCG CTT   2070
His Leu Met His Met Asp Arg Glu Ala Ile Ser Cys Pro Pro Leu
            680             685             690

GGT TCA AAG GGC GTT GGT GGA TTT TGG AAA GCG AAA AAG CGT TAT   2115
Gly Ser Lys Gly Val Gly Gly Phe Trp Lys Ala Lys Lys Arg Tyr
            695             700             705

GCT CTG AAC GTT TAT GAT ATG GAA GAT AAG CGA TTT GCT GAA CCG   2160
Ala Leu Asn Val Tyr Asp Met Glu Asp Lys Arg Phe Ala Glu Pro
            710             715             720

CAT CTA AAA ATC ATG GGT ATG GAA ACT CAG CAG AGT TCA ACA CCA   2205
His Leu Lys Ile Met Gly Met Glu Thr Gln Gln Ser Ser Thr Pro
            725             730             735

AAA GCA GTG CAA GAA GCT CTC GAA GAA AGT ATT CGT CGT ATT CTT   2250
Lys Ala Val Gln Glu Ala Leu Glu Glu Ser Ile Arg Arg Ile Leu
            740             745             750

CAG GAA GGT GAA GAG TCT GTC CAA GAA TAC TAC AAG AAC TTC GAG   2295
Gln Glu Gly Glu Glu Ser Val Gln Glu Tyr Tyr Lys Asn Phe Glu
            755             760             765

AAA GAA TAT CGT CAA CTT GAC TAT AAA GTT ATT GCT GAA GTA AAA   2340
Lys Glu Tyr Arg Gln Leu Asp Tyr Lys Val Ile Ala Glu Val Lys
            770             775             780

ACT GCG AAC GAT ATA GCG AAA TAT GAT GAT AAA GGT TGG CCA GGA   2385
Thr Ala Asn Asp Ile Ala Lys Tyr Asp Asp Lys Gly Trp Pro Gly
            785             790             795

TTT AAA TGC CCG TTC CAT ATT CGT GGT GTG CTA ACT TAT CGT CGA   2430
Phe Lys Cys Pro Phe His Ile Arg Gly Val Leu Thr Tyr Arg Arg
            800             805             810

GCT GTT AGC GGT TTA GGT GTA GCT CCA ATT TTG GAT GGA AAT AAA   2475
Ala Val Ser Gly Leu Gly Val Ala Pro Ile Leu Asp Gly Asn Lys
            815             820             825
```

```
GTA ATG GTT CTT CCA TTA CGT GAA GGA AAT CCA TTT GGT GAC AAG   2520
Val Met Val Leu Pro Leu Arg Glu Gly Asn Pro Phe Gly Asp Lys
            830             835             840

TGC ATT GCT TGG CCA TCG GGT ACA GAA CTT CCA AAA GAA ATT CGT   2565
Cys Ile Ala Trp Pro Ser Gly Thr Glu Leu Pro Lys Glu Ile Arg
            845             850             855

TCT GAT GTG CTA TCT TGG ATT GAC CAC TCA ACT TTG TTC CAA AAA   2610
Ser Asp Val Leu Ser Trp Ile Asp His Ser Thr Leu Phe Gln Lys
            860             865             870

TCG TTT GTT AAA CCG CTT GCG GGT ATG TGT GAA TCG GCT GGC ATG   2655
Ser Phe Val Lys Pro Leu Ala Gly Met Cys Glu Ser Ala Gly Met
            875             880             885

GAC TAT GAA GAA AAA GCT TCG TTA GAC TTC CTG TTT GGC           2694
Asp Tyr Glu Glu Lys Ala Ser Leu Asp Phe Leu Phe Gly
            890             895         898
```

( 2 ) INFORMATION FOR SEQ ID NO:4:

( i ) SEQUENCE CHARACTERISTICS:
        ( A ) LENGTH: 898 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Glu Phe Tyr Ile Ser Ile Glu Thr Val Gly Asn Asn Ile
            5               10              15

Val Glu Arg Tyr Ile Asp Glu Asn Gly Lys Glu Arg Thr Arg Glu
            20              25              30

Val Glu Tyr Leu Pro Thr Met Phe Arg His Cys Lys Glu Glu Ser
            35              40              45

Lys Tyr Lys Asp Ile Tyr Gly Lys Asn Cys Ala Pro Gln Lys Phe
            50              55              60

Pro Ser Met Lys Asp Ala Arg Asp Trp Met Lys Arg Met Glu Asp
            65              70              75

Ile Gly Leu Glu Ala Leu Gly Met Asn Asp Phe Lys Leu Ala Tyr
            80              85              90

Ile Ser Asp Thr Tyr Gly Ser Glu Ile Val Tyr Asp Arg Lys Phe
            95              100             105

Val Arg Val Ala Asn Cys Asp Ile Glu Val Thr Gly Asp Lys Phe
            110             115             120

Pro Asp Pro Met Lys Ala Glu Tyr Glu Ile Asp Ala Ile Thr His
            125             130             135

Tyr Asp Ser Ile Asp Asp Arg Phe Tyr Val Phe Asp Leu Leu Asn
            140             145             150

Ser Met Tyr Gly Ser Val Ser Lys Trp Asp Ala Lys Leu Ala Ala
            155             160             165

Lys Leu Asp Cys Glu Gly Gly Asp Glu Val Pro Gln Glu Ile Leu
            170             175             180

Asp Arg Val Ile Tyr Met Pro Phe Asp Asn Glu Arg Asp Met Leu
            185             190             195

Met Glu Tyr Ile Asn Leu Trp Glu Gln Lys Arg Pro Ala Ile Phe
            200             205             210

Thr Gly Trp Asn Ile Glu Gly Phe Asp Val Pro Tyr Ile Met Asn
            215             220             225

Arg Val Lys Met Ile Leu Gly Glu Arg Ser Met Lys Arg Phe Ser
            230             235             240
```

```
Pro Ile Gly Arg Val Lys Ser Lys Leu Ile Gln Asn Met Tyr Gly
            245                 250                 255
Ser Lys Glu Ile Tyr Ser Ile Asp Gly Val Ser Ile Leu Asp Tyr
            260                 265                 270
Leu Asp Leu Tyr Lys Lys Phe Ala Phe Thr Asn Leu Pro Ser Phe
            275                 280                 285
Ser Leu Glu Ser Val Ala Gln His Glu Thr Lys Lys Gly Lys Leu
            290                 295                 300
Pro Tyr Asp Gly Pro Ile Asn Lys Leu Arg Glu Thr Asn His Gln
            305                 310                 315
Arg Tyr Ile Ser Tyr Asn Ile Ile Asp Val Glu Ser Val Gln Ala
            320                 325                 330
Ile Asp Lys Ile Arg Gly Phe Ile Asp Leu Val Leu Ser Met Ser
            335                 340                 345
Tyr Tyr Ala Lys Met Pro Phe Ser Gly Val Met Ser Pro Ile Lys
            350                 355                 360
Thr Trp Asp Ala Ile Ile Phe Asn Ser Leu Lys Gly Glu His Lys
            365                 370                 375
Val Ile Pro Gln Gln Gly Ser His Val Lys Gln Ser Phe Pro Gly
            380                 385                 390
Ala Phe Val Phe Glu Pro Lys Pro Ile Ala Arg Arg Tyr Ile Met
            395                 400                 405
Ser Phe Asp Leu Thr Ser Leu Tyr Pro Ser Ile Ile Arg Gln Val
            410                 415                 420
Asn Ile Ser Pro Glu Thr Ile Arg Gly Gln Phe Lys Val His Pro
            425                 430                 435
Ile His Glu Tyr Ile Ala Gly Thr Ala Pro Lys Pro Ser Asp Glu
            440                 445                 450
Tyr Ser Cys Ser Pro Asn Gly Trp Met Tyr Asp Lys His Gln Glu
            455                 460                 465
Gly Ile Ile Pro Lys Glu Ile Ala Lys Val Phe Phe Gln Arg Lys
            470                 475                 480
Asp Trp Lys Lys Lys Met Phe Ala Glu Met Asn Ala Glu Ala
            485                 490                 495
Ile Lys Lys Ile Ile Met Lys Gly Ala Gly Ser Cys Ser Thr Lys
            500                 505                 510
Pro Glu Val Glu Arg Tyr Val Lys Phe Ser Asp Asp Phe Leu Asn
            515                 520                 525
Glu Leu Ser Asn Tyr Thr Glu Ser Val Leu Asn Ser Leu Ile Glu
            530                 535                 540
Glu Cys Glu Lys Ala Ala Thr Leu Ala Asn Thr Asn Gln Leu Asn
            545                 550                 555
Arg Lys Ile Leu Ile Asn Ser Leu Tyr Gly Ala Leu Gly Asn Ile
            560                 565                 570
His Phe Arg Tyr Tyr Asp Leu Arg Asn Ala Thr Ala Ile Thr Ile
            575                 580                 585
Phe Gly Gln Val Gly Ile Gln Trp Ile Ala Arg Lys Ile Asn Glu
            590                 595                 600
Tyr Leu Asn Lys Val Cys Gly Thr Asn Asp Glu Asp Phe Ile Ala
            605                 610                 615
Ala Gly Asp Thr Asp Ser Val Tyr Val Cys Val Asp Lys Val Ile
            620                 625                 630
Glu Lys Val Gly Leu Asp Arg Phe Lys Glu Gln Asn Asp Leu Val
            635                 640                 645
```

```
Glu  Phe  Met  Asn  Gln  Phe  Gly  Lys  Lys  Lys  Met  Glu  Pro  Met  Ile
               650                      655                      660

Asp  Val  Ala  Tyr  Arg  Glu  Leu  Cys  Asp  Tyr  Met  Asn  Asn  Arg  Glu
               665                      670                      675

His  Leu  Met  His  Met  Asp  Arg  Glu  Ala  Ile  Ser  Cys  Pro  Pro  Leu
               680                      685                      690

Gly  Ser  Lys  Gly  Val  Gly  Gly  Phe  Trp  Lys  Ala  Lys  Lys  Arg  Tyr
               695                      700                      705

Ala  Leu  Asn  Val  Tyr  Asp  Met  Glu  Asp  Lys  Arg  Phe  Ala  Glu  Pro
               710                      715                      720

His  Leu  Lys  Ile  Met  Gly  Met  Glu  Thr  Gln  Gln  Ser  Ser  Thr  Pro
               725                      730                      735

Lys  Ala  Val  Gln  Glu  Ala  Leu  Glu  Glu  Ser  Ile  Arg  Arg  Ile  Leu
               740                      745                      750

Gln  Glu  Gly  Glu  Glu  Ser  Val  Gln  Glu  Tyr  Tyr  Lys  Asn  Phe  Glu
               755                      760                      765

Lys  Glu  Tyr  Arg  Gln  Leu  Asp  Tyr  Lys  Val  Ile  Ala  Glu  Val  Lys
               770                      775                      780

Thr  Ala  Asn  Asp  Ile  Ala  Lys  Tyr  Asp  Lys  Gly  Trp  Pro  Gly
               785                      790                      795

Phe  Lys  Cys  Pro  Phe  His  Ile  Arg  Gly  Val  Leu  Thr  Tyr  Arg  Arg
               800                      805                      810

Ala  Val  Ser  Gly  Leu  Gly  Val  Ala  Pro  Ile  Leu  Asp  Gly  Asn  Lys
               815                      820                      825

Val  Met  Val  Leu  Pro  Leu  Arg  Glu  Gly  Asn  Pro  Phe  Gly  Asp  Lys
               830                      835                      840

Cys  Ile  Ala  Trp  Pro  Ser  Gly  Thr  Glu  Leu  Pro  Lys  Glu  Ile  Arg
               845                      850                      855

Ser  Asp  Val  Leu  Ser  Trp  Ile  Asp  His  Ser  Thr  Leu  Phe  Gln  Lys
               860                      865                      870

Ser  Phe  Val  Lys  Pro  Leu  Ala  Gly  Met  Cys  Glu  Ser  Ala  Gly  Met
               875                      880                      885

Asp  Tyr  Glu  Glu  Lys  Ala  Ser  Leu  Asp  Phe  Leu  Phe  Gly
               890                      895           898
```

( 2 ) INFORMATION FOR SEQ ID NO:5:

( i ) SEQUENCE CHARACTERISTICS:
        ( A ) LENGTH: 2459 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 108..2456

( x i ) SEQUENCE DESCRIPTION: SEQ ID NO:5:

```
AAGCATGGCG  CGAAGGCATA  TTACGGGCAG  TAATGACTGT  ATAAAACCAC         50

AGCCAATCAA  ACGAAACCAG  GCTATACTCA  AGCCTGGTTT  TTTGATGGAT        100

TTTCAGC  GTG  GCG  CAG  GCA  GGT  TTT  ATC  TTA  ACC  CGA          137
         Val  Ala  Gln  Ala  Gly  Phe  Ile  Leu  Thr  Arg
                         5                        10

CAC  TGG  CGG  GAC  ACC  CCG  CAA  GGG  ACA  GAA  GTC  TCC  TTC  TGG  CTG   182
His  Trp  Arg  Asp  Thr  Pro  Gln  Gly  Thr  Glu  Val  Ser  Phe  Trp  Leu
               15                       20                       25
```

| | | | | | | | | | | | | | | |
|---|---|---|---|---|---|---|---|---|---|---|---|---|---|---|
| GCG | ACG | GAC | AAC | GGG | CCG | TTG | CAG | GTT | ACG | CTT | GCA | CCG | CAA | GAG | 227 |
| Ala | Thr | Asp | Asn | Gly<br>30 | Pro | Leu | Gln | Val | Thr<br>35 | Leu | Ala | Pro | Gln | Glu<br>40 |

```
GCG ACG GAC AAC GGG CCG TTG CAG GTT ACG CTT GCA CCG CAA GAG   227
Ala Thr Asp Asn Gly Pro Leu Gln Val Thr Leu Ala Pro Gln Glu
             30              35                      40

TCC GTG GCG TTT ATT CCC GCC GAT CAG GTT CCC CGC GCT CAG CAT   272
Ser Val Ala Phe Ile Pro Ala Asp Gln Val Pro Arg Ala Gln His
             45              50                      55

ATT TTG CAG GGT GAA CAA GGC TTT CGC CTG ACA CCG CTG GCG TTA   317
Ile Leu Gln Gly Glu Gln Gly Phe Arg Leu Thr Pro Leu Ala Leu
             60              65                      70

AAG GAT TTT CAC CGC CAG CCG GTG TAT GGC CTT TAC TGT CGC GCC   362
Lys Asp Phe His Arg Gln Pro Val Tyr Gly Leu Tyr Cys Arg Ala
             75              80                      85

CAT CGC CAA TTG ATG AAT TAC GAA AAG CGC CTG CGT GAA GGT GGC   407
His Arg Gln Leu Met Asn Tyr Glu Lys Arg Leu Arg Glu Gly Gly
             90              95                     100

GTT ACC GTC TAC GAG GCC GAT GTG CGT CCG CCA GAA CGC TAT CTG   452
Val Thr Val Tyr Glu Ala Asp Val Arg Pro Pro Glu Arg Tyr Leu
            105             110                     115

ATG GAG CGG TTT ATC ACC TCA CCG GTG TGG GTC GAG GGT GAT ATG   497
Met Glu Arg Phe Ile Thr Ser Pro Val Trp Val Glu Gly Asp Met
            120             125                     130

CAC AAT GGC ACT ATC GTT AAT GCC CGT CTG AAA CCG CAT CCC GAC   542
His Asn Gly Thr Ile Val Asn Ala Arg Leu Lys Pro His Pro Asp
            135             140                     145

TAT CGT CCG CCG CTC AAG TGG GTT TCT ATA GAT ATT GAA ACC ACC   587
Tyr Arg Pro Pro Leu Lys Trp Val Ser Ile Asp Ile Glu Thr Thr
            150             155                     160

CGC CAC GGT GAG CTG TAC TGC ATC GGC CTG GAA GGC TGC GGG CAG   632
Arg His Gly Glu Leu Tyr Cys Ile Gly Leu Glu Gly Cys Gly Gln
            165             170                     175

CGC ATC GTT TAT ATG CTG GGG CCG GAG AAT GGC GAC GCC TCC TCG   677
Arg Ile Val Tyr Met Leu Gly Pro Glu Asn Gly Asp Ala Ser Ser
            180             185                     190

CTT GAT TTC GAA CTG GAA TAC GTC GCC AGC CGC CCG CAG TTG CTG   722
Leu Asp Phe Glu Leu Glu Tyr Val Ala Ser Arg Pro Gln Leu Leu
            195             200                     205

GAA AAA CTC AAC GCC TGG TTT GCC AAC TAC GAT CCT GAT GTG ATC   767
Glu Lys Leu Asn Ala Trp Phe Ala Asn Tyr Asp Pro Asp Val Ile
            210             215                     220

ATC GGT TGG AAC GTG GTG CAG TTC GAT CTG CGA ATG CTG CAA AAA   812
Ile Gly Trp Asn Val Val Gln Phe Asp Leu Arg Met Leu Gln Lys
            225             230                     235

CAT GCC GAG CGT TAC CGT CTT CCG CTG CGT CTT GGG CGC GAT AAT   857
His Ala Glu Arg Tyr Arg Leu Pro Leu Arg Leu Gly Arg Asp Asn
            240             245                     250

AGC GAG CTG GAG TGG CGC GAC GAC GGC TTT AAA AAC GGC GTC TTT   902
Ser Glu Leu Glu Trp Arg Asp Asp Gly Phe Lys Asn Gly Val Phe
            255             260                     265

TTT GCC CAG GCT AAA GGT GGG CTA ATT ATC GAC GGT ATC GAG GCG   947
Phe Ala Gln Ala Lys Gly Gly Leu Ile Ile Asp Gly Ile Glu Ala
            270             275                     280

CTG AAA TCC GCG TTC TGG AAT TTC TCT TCA TTC TCG CTG GAA ACT   992
Leu Lys Ser Ala Phe Trp Asn Phe Ser Ser Phe Ser Leu Glu Thr
            285             290                     295

GTC GCT CAG GAG CTA TTA GGC GAA GGA AAA TCT ATC GAT AAC CCG  1037
Val Ala Gln Glu Leu Leu Gly Glu Gly Lys Ser Ile Asp Asn Pro
            300             305                     310

TGG GAT CGA ATG GAC GAA ATT GAC CGC CGT TTC GCC GAA GAT AAA  1082
Trp Asp Arg Met Asp Glu Ile Asp Arg Arg Phe Ala Glu Asp Lys
            315             320                     325
```

```
CCT GCG CTG GCA ACT TAT AAC CTG AAA GAT TGC GAG CTG GTG ACG    1127
Pro Ala Leu Ala Thr Tyr Asn Leu Lys Asp Cys Glu Leu Val Thr
                330                 335                 340

CAG ATC TTC CAC AAA ACT GAA ATC ATG CCA TTT TTA CTC GAA CGG    1172
Gln Ile Phe His Lys Thr Glu Ile Met Pro Phe Leu Leu Glu Arg
                345                 350                 355

GCA ACG GTG AAC GGC CTG CCG GTG GAC CGA CAC GGC GGT TCG GTG    1217
Ala Thr Val Asn Gly Leu Pro Val Asp Arg His Gly Gly Ser Val
                360                 365                 370

GCG GCA TTT GGT CAT CTC TAT TTT CCG CGA ATG CAT CGC GCT GGT    1262
Ala Ala Phe Gly His Leu Tyr Phe Pro Arg Met His Arg Ala Gly
                375                 380                 385

TAT GTC GCG CCT AAT CTC GGC GAA GTG CCG CCG CAC GCC AGC CCT    1307
Tyr Val Ala Pro Asn Leu Gly Glu Val Pro Pro His Ala Ser Pro
                390                 395                 400

GGC GGC TAC GTG ATG GAT TCA CGG CCA GGG CTT TAT GAT TCA GTG    1352
Gly Gly Tyr Val Met Asp Ser Arg Pro Gly Leu Tyr Asp Ser Val
                405                 410                 415

CTG GTG CTG GAC TAT AAA AGC CTG TAC CCG TCG ATC ATC CGC ACC    1397
Leu Val Leu Asp Tyr Lys Ser Leu Tyr Pro Ser Ile Ile Arg Thr
                420                 425                 430

TTT CTG ATT GAT CCC GTC GGG CTG GTG GAA GGC ATG GCG CAG CCT    1442
Phe Leu Ile Asp Pro Val Gly Leu Val Glu Gly Met Ala Gln Pro
                435                 440                 445

GAT CCA GAG CAC AGT ACC GAA GGT TTT CTC GAT GCC TGG TTC TCG    1487
Asp Pro Glu His Ser Thr Glu Gly Phe Leu Asp Ala Trp Phe Ser
                450                 455                 460

CGA GAA AAA CAT TGC CTG CCG GAG ATT GTG ACT AAC ATC TGG CAC    1532
Arg Glu Lys His Cys Leu Pro Glu Ile Val Thr Asn Ile Trp His
                465                 470                 475

GGG CGC GAT GAA GCC AAA CGC CAG GGT AAC AAA CCG CTG TCG CAG    1577
Gly Arg Asp Glu Ala Lys Arg Gln Gly Asn Lys Pro Leu Ser Gln
                480                 485                 490

GCG CTG AAA ATC ATC ATG AAT GCC TTT TAT GGC GTG CTC GGC ACC    1622
Ala Leu Lys Ile Ile Met Asn Ala Phe Tyr Gly Val Leu Gly Thr
                495                 500                 505

ACC GCC TGC CGC TTC TTC GAT CCG CGG CTG GCA TCG TCG ATC ACC    1667
Thr Ala Cys Arg Phe Phe Asp Pro Arg Leu Ala Ser Ser Ile Thr
                510                 515                 520

ATG CGT GGT CAT CAG ATC ATG CGG CAA ACC AAA GCG TTG ATT GAA    1712
Met Arg Gly His Gln Ile Met Arg Gln Thr Lys Ala Leu Ile Glu
                525                 530                 535

GCA CAG GGC TAC GAC GTT ATC TAC GGC GAT ACC GAC TCA ACG TTT    1757
Ala Gln Gly Tyr Asp Val Ile Tyr Gly Asp Thr Asp Ser Thr Phe
                540                 545                 550

GTC TGG CTG AAA GGC GCA CAT TCG GAA GAA GAA GCG GCG AAA ATC    1802
Val Trp Leu Lys Gly Ala His Ser Glu Glu Glu Ala Ala Lys Ile
                555                 560                 565

GGT CGT GCA CTG GTG CAG CAC GTT AAC GCC TGG TGG GCG GAA ACG    1847
Gly Arg Ala Leu Val Gln His Val Asn Ala Trp Trp Ala Glu Thr
                570                 575                 580

CTG CAA AAA CAA CGG CTG ACC AGC GCA TTA GAA CTG GAG TAT GAA    1892
Leu Gln Lys Gln Arg Leu Thr Ser Ala Leu Glu Leu Glu Tyr Glu
                585                 590                 595

ACC CAT TTC TGC CGT TTT CTG ATG CCA ACC ATT CGC GGA GCC GAT    1937
Thr His Phe Cys Arg Phe Leu Met Pro Thr Ile Arg Gly Ala Asp
                600                 605                 610

ACC GGC AGT AAA AAG CGT TAT GCC GGA CTG ATT CAG GAG GGC GAC    1982
Thr Gly Ser Lys Lys Arg Tyr Ala Gly Leu Ile Gln Glu Gly Asp
                615                 620                 625
```

```
AAG  CAG  CGG  ATG  GTG  TTT  AAA  GGG  CTG  GAA  ACC  GTG  CGC  ACC  GAC   2027
Lys  Gln  Arg  Met  Val  Phe  Lys  Gly  Leu  Glu  Thr  Val  Arg  Thr  Asp
               630                 635                           640

TGG  ACG  CCG  CTG  GCC  CAG  CAG  TTT  CAG  CAG  GAG  CTA  TAC  CTG  CGC   2072
Trp  Thr  Pro  Leu  Ala  Gln  Gln  Phe  Gln  Gln  Glu  Leu  Tyr  Leu  Arg
               645                 650                           655

ATC  TTC  CGC  AAC  GAG  CCA  TAT  CAG  GAA  TAT  GTA  CGC  GAA  ACC  ATC   2117
Ile  Phe  Arg  Asn  Glu  Pro  Tyr  Gln  Glu  Tyr  Val  Arg  Glu  Thr  Ile
               660                 665                           670

GAC  AAA  CTG  ATG  GCG  GGT  GAA  CTG  GAT  GCG  CGA  CTG  GTT  TAC  CGT   2162
Asp  Lys  Leu  Met  Ala  Gly  Glu  Leu  Asp  Ala  Arg  Leu  Val  Tyr  Arg
               675                 680                           685

AAA  CGC  CTT  CGC  CGT  CCG  CTG  AGC  GAG  TAT  CAG  CGT  AAT  GTG  CCG   2207
Lys  Arg  Leu  Arg  Arg  Pro  Leu  Ser  Glu  Tyr  Gln  Arg  Asn  Val  Pro
               690                 695                           700

CCT  CAT  GTA  CGC  GCC  GCT  CGC  CTT  GCC  GAT  GAA  GAA  AAC  CAA  AAG   2252
Pro  His  Val  Arg  Ala  Ala  Arg  Leu  Ala  Asp  Glu  Glu  Asn  Gln  Lys
               705                 710                           715

CGT  GGT  CGC  CCC  TTG  CAA  TAT  CAG  AAT  CGC  GGC  ACC  ATT  AAG  TAC   2297
Arg  Gly  Arg  Pro  Leu  Gln  Tyr  Gln  Asn  Arg  Gly  Thr  Ile  Lys  Tyr
               720                 725                           730

GTA  TGG  ACC  ACC  AAC  GGC  CCG  GAG  CCG  CTG  GAC  TAC  CAA  CGT  TCA   2342
Val  Trp  Thr  Thr  Asn  Gly  Pro  Glu  Pro  Leu  Asp  Tyr  Gln  Arg  Ser
               735                 740                           745

CCA  CTG  GAT  TAC  GAA  CAC  TAT  CTG  ACC  CGC  CAG  CTA  CAA  CCC  GTG   2387
Pro  Leu  Asp  Tyr  Glu  His  Tyr  Leu  Thr  Arg  Gln  Leu  Gln  Pro  Val
               750                 755                           760

GCG  GAG  GGA  ATA  CTC  CCT  TTT  ATT  GAG  GAT  AAT  TTT  GCT  ACA  CTT   2432
Ala  Glu  Gly  Ile  Leu  Pro  Phe  Ile  Glu  Asp  Asn  Phe  Ala  Thr  Leu
               765                 770                           775

ATG  ACC  GGG  CAA  CTT  GGG  CTA  TTT  TGA                                 2459
Met  Thr  Gly  Gln  Leu  Gly  Leu  Phe
               780            783
```

( 2 ) INFORMATION FOR SEQ ID NO:6:

( i ) SEQUENCE CHARACTERISTICS:
        ( A ) LENGTH: 783 base pairs
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Val  Ala  Gln  Ala  Gly  Phe  Ile  Leu  Thr  Arg  His  Trp  Arg  Asp  Thr
                    5                   10                          15

Pro  Gln  Gly  Thr  Glu  Val  Ser  Phe  Trp  Leu  Ala  Thr  Asp  Asn  Gly
                    20                  25                          30

Pro  Leu  Gln  Val  Thr  Leu  Ala  Pro  Gln  Glu  Ser  Val  Ala  Phe  Ile
                    35                  40                          45

Pro  Ala  Asp  Gln  Val  Pro  Arg  Ala  Gln  His  Ile  Leu  Gln  Gly  Glu
                    50                  55                          60

Gln  Gly  Phe  Arg  Leu  Thr  Pro  Leu  Ala  Leu  Lys  Asp  Phe  His  Arg
                    65                  70                          75

Gln  Pro  Val  Tyr  Gly  Leu  Tyr  Cys  Arg  Ala  His  Arg  Gln  Leu  Met
                    80                  85                          90

Asn  Tyr  Glu  Lys  Arg  Leu  Arg  Glu  Gly  Gly  Val  Thr  Val  Tyr  Glu
                    95                  100                         105

Ala  Asp  Val  Arg  Pro  Pro  Glu  Arg  Tyr  Leu  Met  Glu  Arg  Phe  Ile
                    110                 115                         120
```

-continued

| | | | | | | | | | | | | | | |
|---|---|---|---|---|---|---|---|---|---|---|---|---|---|---|
|Thr|Ser|Pro|Val|Trp|Val|Glu|Gly|Asp|Met|His|Asn|Gly|Thr|Ile|
| | | | |125| | | |130| | | | |135| |
|Val|Asn|Ala|Arg|Leu|Lys|Pro|His|Pro|Asp|Tyr|Arg|Pro|Pro|Leu|
| | | |140| | | | |145| | | | |150| |
|Lys|Trp|Val|Ser|Ile|Asp|Ile|Glu|Thr|Thr|Arg|His|Gly|Glu|Leu|
| | | | |155| | | |160| | | | |165| |
|Tyr|Cys|Ile|Gly|Leu|Glu|Gly|Cys|Gly|Gln|Arg|Ile|Val|Tyr|Met|
| | | | |170| | | |175| | | | |180| |
|Leu|Gly|Pro|Glu|Asn|Gly|Asp|Ala|Ser|Ser|Leu|Asp|Phe|Glu|Leu|
| | | | |185| | | |190| | | | |195| |
|Glu|Tyr|Val|Ala|Ser|Arg|Pro|Gln|Leu|Leu|Glu|Lys|Leu|Asn|Ala|
| | | | |200| | | |205| | | | |210| |
|Trp|Phe|Ala|Asn|Tyr|Asp|Pro|Asp|Val|Ile|Ile|Gly|Trp|Asn|Val|
| | | | |215| | | |220| | | | |225| |
|Val|Gln|Phe|Asp|Leu|Arg|Met|Leu|Gln|Lys|His|Ala|Glu|Arg|Tyr|
| | | | |230| | | |235| | | | |240| |
|Arg|Leu|Pro|Leu|Arg|Leu|Gly|Arg|Asp|Asn|Ser|Glu|Leu|Glu|Trp|
| | | | |245| | | |250| | | | |255| |
|Arg|Asp|Asp|Gly|Phe|Lys|Asn|Gly|Val|Phe|Phe|Ala|Gln|Ala|Lys|
| | | | |260| | | |265| | | | |270| |
|Gly|Gly|Leu|Ile|Ile|Asp|Gly|Ile|Glu|Ala|Leu|Lys|Ser|Ala|Phe|
| | | | |275| | | |280| | | | |285| |
|Trp|Asn|Phe|Ser|Ser|Phe|Ser|Leu|Glu|Thr|Val|Ala|Gln|Glu|Leu|
| | | | |290| | | |295| | | | |300| |
|Leu|Gly|Glu|Gly|Lys|Ser|Ile|Asp|Asn|Pro|Trp|Asp|Arg|Met|Asp|
| | | | |305| | | |310| | | | |315| |
|Glu|Ile|Asp|Arg|Arg|Phe|Ala|Glu|Asp|Lys|Pro|Ala|Leu|Ala|Thr|
| | | | |320| | | |325| | | | |330| |
|Tyr|Asn|Leu|Lys|Asp|Cys|Glu|Leu|Val|Thr|Gln|Ile|Phe|His|Lys|
| | | | |335| | | |340| | | | |345| |
|Thr|Glu|Ile|Met|Pro|Phe|Leu|Leu|Glu|Arg|Ala|Thr|Val|Asn|Gly|
| | | | |350| | | |355| | | | |360| |
|Leu|Pro|Val|Asp|Arg|His|Gly|Gly|Ser|Val|Ala|Ala|Phe|Gly|His|
| | | | |365| | | |370| | | | |375| |
|Leu|Tyr|Phe|Pro|Arg|Met|His|Arg|Ala|Gly|Tyr|Val|Ala|Pro|Asn|
| | | | |380| | | |385| | | | |390| |
|Leu|Gly|Glu|Val|Pro|Pro|His|Ala|Ser|Pro|Gly|Gly|Tyr|Val|Met|
| | | | |395| | | |400| | | | |405| |
|Asp|Ser|Arg|Pro|Gly|Leu|Tyr|Asp|Ser|Val|Leu|Val|Leu|Asp|Tyr|
| | | | |410| | | |415| | | | |420| |
|Lys|Ser|Leu|Tyr|Pro|Ser|Ile|Ile|Arg|Thr|Phe|Leu|Ile|Asp|Pro|
| | | | |425| | | |430| | | | |435| |
|Val|Gly|Leu|Val|Glu|Gly|Met|Ala|Gln|Pro|Asp|Pro|Glu|His|Ser|
| | | | |440| | | |445| | | | |450| |
|Thr|Glu|Gly|Phe|Leu|Asp|Ala|Trp|Phe|Ser|Arg|Glu|Lys|His|Cys|
| | | | |455| | | |460| | | | |465| |
|Leu|Pro|Glu|Ile|Val|Thr|Asn|Ile|Trp|His|Gly|Arg|Asp|Glu|Ala|
| | | | |470| | | |475| | | | |480| |
|Lys|Arg|Gln|Gly|Asn|Lys|Pro|Leu|Ser|Gln|Ala|Leu|Lys|Ile|Ile|
| | | | |485| | | |490| | | | |495| |
|Met|Asn|Ala|Phe|Tyr|Gly|Val|Leu|Gly|Thr|Thr|Ala|Cys|Arg|Phe|
| | | | |500| | | |505| | | | |510| |
|Phe|Asp|Pro|Arg|Leu|Ala|Ser|Ser|Ile|Thr|Met|Arg|Gly|His|Gln|

|     |     |     |     | 515 |     |     |     | 520 |     |     |     | 525 |
|-----|-----|-----|-----|-----|-----|-----|-----|-----|-----|-----|-----|-----|
| Ile | Met | Arg | Gln | Thr | Lys | Ala | Leu | Ile | Glu | Ala | Gln | Gly | Tyr | Asp |
|     |     |     |     | 530 |     |     |     | 535 |     |     |     | 540 |
| Val | Ile | Tyr | Gly | Asp | Thr | Asp | Ser | Thr | Phe | Val | Trp | Leu | Lys | Gly |
|     |     |     |     | 545 |     |     |     | 550 |     |     |     | 555 |
| Ala | His | Ser | Glu | Glu | Glu | Ala | Ala | Lys | Ile | Gly | Arg | Ala | Leu | Val |
|     |     |     |     | 560 |     |     |     | 565 |     |     |     | 570 |
| Gln | His | Val | Asn | Ala | Trp | Trp | Ala | Glu | Thr | Leu | Gln | Lys | Gln | Arg |
|     |     |     |     | 575 |     |     |     | 580 |     |     |     | 585 |
| Leu | Thr | Ser | Ala | Leu | Glu | Leu | Glu | Tyr | Glu | Thr | His | Phe | Cys | Arg |
|     |     |     |     | 590 |     |     |     | 595 |     |     |     | 600 |
| Phe | Leu | Met | Pro | Thr | Ile | Arg | Gly | Ala | Asp | Thr | Gly | Ser | Lys | Lys |
|     |     |     |     | 605 |     |     |     | 610 |     |     |     | 615 |
| Arg | Tyr | Ala | Gly | Leu | Ile | Gln | Glu | Gly | Asp | Lys | Gln | Arg | Met | Val |
|     |     |     |     | 620 |     |     |     | 625 |     |     |     | 630 |
| Phe | Lys | Gly | Leu | Glu | Thr | Val | Arg | Thr | Asp | Trp | Thr | Pro | Leu | Ala |
|     |     |     |     | 635 |     |     |     | 640 |     |     |     | 645 |
| Gln | Gln | Phe | Gln | Gln | Glu | Leu | Tyr | Leu | Arg | Ile | Phe | Arg | Asn | Glu |
|     |     |     |     | 650 |     |     |     | 655 |     |     |     | 660 |
| Pro | Tyr | Gln | Glu | Tyr | Val | Arg | Glu | Thr | Ile | Asp | Lys | Leu | Met | Ala |
|     |     |     |     | 665 |     |     |     | 670 |     |     |     | 675 |
| Gly | Glu | Leu | Asp | Ala | Arg | Leu | Val | Tyr | Arg | Lys | Arg | Leu | Arg | Arg |
|     |     |     |     | 680 |     |     |     | 685 |     |     |     | 690 |
| Pro | Leu | Ser | Glu | Tyr | Gln | Arg | Asn | Val | Pro | Pro | His | Val | Arg | Ala |
|     |     |     |     | 695 |     |     |     | 700 |     |     |     | 705 |
| Ala | Arg | Leu | Ala | Asp | Glu | Glu | Asn | Gln | Lys | Arg | Gly | Arg | Pro | Leu |
|     |     |     |     | 710 |     |     |     | 715 |     |     |     | 720 |
| Gln | Tyr | Gln | Asn | Arg | Gly | Thr | Ile | Lys | Tyr | Val | Trp | Thr | Thr | Asn |
|     |     |     |     | 725 |     |     |     | 730 |     |     |     | 735 |
| Gly | Pro | Glu | Pro | Leu | Asp | Tyr | Gln | Arg | Ser | Pro | Leu | Asp | Tyr | Glu |
|     |     |     |     | 740 |     |     |     | 745 |     |     |     | 750 |
| His | Tyr | Leu | Thr | Arg | Gln | Leu | Gln | Pro | Val | Ala | Glu | Gly | Ile | Leu |
|     |     |     |     | 755 |     |     |     | 760 |     |     |     | 765 |
| Pro | Phe | Ile | Glu | Asp | Asn | Phe | Ala | Thr | Leu | Met | Thr | Gly | Gln | Leu |
|     |     |     |     | 770 |     |     |     | 775 |     |     |     | 780 |
| Gly | Leu | Phe |     |     |     |     |     |     |     |     |     |     |
|     |     | 783 |     |     |     |     |     |     |     |     |     |     |